ical Structures of Immunoglobulins", J. Mol. Biol., 273:927-948.

United States Patent
Baum et al.

(10) Patent No.: US 11,773,156 B2
(45) Date of Patent: Oct. 3, 2023

(54) ANTI-HEMAGGLUTININ ANTIBODIES AND METHODS OF USE THEREOF

(71) Applicant: REGENERON PHARMACEUTICALS, INC., Tarrytown, NY (US)

(72) Inventors: Alina Baum, Pleasantville, NY (US); Christos Kyratsous, Irvington, NY (US)

(73) Assignee: REGENERON PHARMACEUTICALS, INC., Tarrytown, NY (US)

( * ) Notice: Subject to any disclaimer, the term of this patent is extended or adjusted under 35 U.S.C. 154(b) by 381 days.

(21) Appl. No.: 17/082,375

(22) Filed: Oct. 28, 2020

(65) Prior Publication Data

US 2021/0171612 A1    Jun. 10, 2021

Related U.S. Application Data

(60) Provisional application No. 63/094,170, filed on Oct. 20, 2020, provisional application No. 62/926,914, filed on Oct. 28, 2019.

(51) Int. Cl.
*C07K 16/10* (2006.01)
*A61P 31/16* (2006.01)
*A61K 45/06* (2006.01)

(52) U.S. Cl.
CPC .......... *C07K 16/1018* (2013.01); *A61K 45/06* (2013.01); *A61P 31/16* (2018.01)

(58) Field of Classification Search
None
See application file for complete search history.

(56) References Cited

U.S. PATENT DOCUMENTS

| | | | |
|---|---|---|---|
| 6,596,541 B2 | 7/2003 | Murphy et al. | |
| 7,582,298 B2 | 9/2009 | Stevens et al. | |
| 8,246,995 B2 | 8/2012 | Dai et al. | |
| 8,257,740 B1 | 9/2012 | Sung et al. | |
| 9,359,437 B2 | 6/2016 | Davis et al. | |
| 10,143,186 B2 | 12/2018 | McWhirter et al. | |
| 2004/0101920 A1 | 5/2004 | Radziejewski et al. | |
| 2010/0331527 A1 | 12/2010 | Davis et al. | |
| 2013/0247234 A1* | 9/2013 | Mcwhirter | C07K 16/00 435/71.1 |
| 2015/0274812 A1 | 10/2015 | Swem et al. | |
| 2017/0189529 A1 | 7/2017 | Estelles et al. | |

FOREIGN PATENT DOCUMENTS

| | | |
|---|---|---|
| EP | 3305811 | 4/2018 |
| WO | WO 2005103081 | 11/2005 |
| WO | WO 2013/114885 | 8/2013 |
| WO | WO 2015/120097 | 8/2015 |
| WO | WO 2016/011035 | 1/2016 |
| WO | WO 2016/196470 | 12/2016 |

OTHER PUBLICATIONS

Almagro & Fransson, Frontiers in Bioscience 2008; 13:1619-33 (Year: 2008).*
Lim, et al. (2017) "A Phase 1, Randomized, Double-Blind, Placebo-Controlled, Single-Ascending-Dose Study To Investigate the Safety, Tolerability, and Pharmacokinetics of an Anti-Influenza B Virus Monoclonal Antibody, MHAB5553A, in Healthy Volunteers", Antimicrobial Agents and Chemotherapy, 61(8):e00279-17.
Padilla-Quirarte, et al. (2019) "Protective Antibodies Against Influenza Proteins", Frontiers in Immunology, 10: Article 1677.
Shen, et al. (2017) ""A Multimechanistic Antibody Targeting the ReceptorBinding Site Potently Cross-Protects Against Influenza B Viruses"", Science Translation Medicine, 9(412):eaam5752.
Tan, et al. (2018) "Universal influenza Virus Vaccines and Therapeutics: Where Do We Stand With Influenza B Virus?", Current Opinion in Immunology, 53:45-50.
Wohlbold, et al. (2017) "Broadly Protective Murine Monoclonal Antibodies Against Influenza B Virus Target Highly Conserved Neuraminidase Epitopes", Nature Microbiology, 2(10):1415-1424.
Yasugi et al. (2013) "Human Monoclonal Antibodies Broadly Neutralizing Against Influenza B Virus," PLoS Pathog, 9(2): e1003150.
International Search Report and Written Opinion for International application No. PCT US2020/057635 dated Mar. 23, 2021, 22 pages.
Abdiche et al. (2008) "Determining Kinetics and Affinities of Protein Interactions Using a Parallel Real-Time Label-Free Biosensor, the Octet", Analytical Biochemistry, 377(2), 209-217.
Al-Lazikani et al. (1997) "Standard Conformations for the Canonical Structures of Immunoglobulins", J. Mol. Biol., 273:927-948.
Allen (1999) "The Art, Science and Technology of Pharmaceutical Compounding", Fifth Edition, American Pharmacists Association, Washington D.C.
Altschul et al. (1990) "Basic Local Alignment Search Tool", J. Mol. Biol., 215: 403-410.
Arruebo et al. (2009) "Antibody-Conjugated Nanoparticles for Biomedical Applications", J. Nanomat., vol. 2009, Article ID 439389, 24 pages, doi: 10.1155/2009/439389.
Ehring (1999) "Hydrogen Exchange/Electrospray Ionization Mass Spectrometry Studies of Structural Features of Proteins and Protein/Protein Interactions", Analytical Biochemistry, 267: 252-259.

(Continued)

*Primary Examiner* — Peter J Reddig
(74) *Attorney, Agent, or Firm* — FisherBroyles, LLP; Cara L. Crowley-Weber; Gabriele Amodeo

(57) ABSTRACT

Provided herein are monoclonal antibodies, or antigen-binding fragments thereof, that bind to the influenza B hemagglutinin (HA) protein, pharmaceutical compositions comprising the antibodies and methods of use. The antibodies are useful for inhibiting or neutralizing influenza B virus activity, thus providing a means of treating or preventing influenza infection in humans. Also provided is the use of one or more antibodies that bind to the influenza B HA for preventing viral attachment and/or entry into host cells. The antibodies may be used prophylactically or therapeutically and may be used alone or in combination with one or more other anti-viral agents or vaccines.

21 Claims, No Drawings

Specification includes a Sequence Listing.

(56) References Cited

OTHER PUBLICATIONS

Engen and Smith (2001) "The Basics of Ion Chromatography, Metrohm 792 Basic IC", Anal. Chem., 73: 256A-265A.
Gonnet et al. (1992) "Exhaustive Matching of the Entire Protein Sequence Database", Science, 256:1443 1445.
Good et al. (1991) "Historic Aspects of Intravenous Immunoglobulin Therapy", Cancer, 68:1415-1421.
Harlow and Lane (2014) "Antibodies", A Laboratory Manual, Second Edition, Cold Spring Harbor Press, Cold Spring Harbor, NY.
Junghans et al. (1990) "Anti-Tac-H, a Humanized Antibody to the Interleukin 2 Receptor with New Features for Immunotherapy in Malignant and Immune Disorders", Cancer Res., 50:1495-1502.
Kabat (1991) "Sequences of Proteins of Immunological Interest," National Institutes of Health, Bethesda, Md.
Kazane et al. (2012) "Synthesis of Bispecific Antibodies Using Genetically Enclosed Unnatural Amino Acids", J. Am. Chem. Soc., 134:9918-9921.
Klein et al. (2012) "Progress in Overcoming the Chain Association Issue in Bispecific Heterodimeric IgG Antibodies", mAbs, 4(6):653-663.
Kufer et al. (2004) "A Revival of Bispectific Antibodies", Trends Biotechnol., 22:238-244.
Langer (1990) "New Methods of Drug Delivery", Science, 249:1527-1533.
Marasco et al. (2007) "The Growth and Potential of Human Antiviral Monoclonal Antibody Therapeutics", Nature Biotechnology, 25(12):1421-1434.
Martin et al. (1989) "Modeling Antibody Hypervariable Loops: A Combined Algorithm", Proc. Natl. Acad. Sci. USA, 86:9268-9272.
Padlan et al. (1995) "Identification of Specificity-Determining Residues in Antibodies", FASEB J., 9:133-139.
Pearson (1994) "Using the FASTA Program to Search Protein and DNA Sequence Databases", Methods Mol. Biol., 24: 307-331.
Pearson (2000) "Flexible Sequence Similarity Searching with the FASTA3 Program Package", Methods in Mol. Biol., 132:185-219.
Powell et al. (1998) "Compendium of Excipients for Parenteral Formulations", PDA J Pharm Sci Technol, 52:238-311.
Reddy et al. (2000), "Elimination of Fc Receptor-Dependent Effector Functions of a Modified IgG4 Monoclonal Antibody to Human CD4", J. Immunol., 164:1925-1933.
Reineke (2004) "Antibody Epitope Mapping Using Arrays of Synthetic Peptides", Methods Mol. Biol., 248: 443-463.
Tomer (2000) "Characterization of a Discontinuous Epitope of the Human Immunodeficiency Virus (HIV) Core Protein p24 by Epitope Excision and Differential Chemical Modification Followed by Mass Spectrometric Peptide Mapping Analysis", Prot. Sci., 9: 487-496.
Tutt et al. (1991) "Trispecific F(ab')3 Derivatives that use Cooperative Signaling Via the TCR/CD3 Complex and CD2 to Activate and Redirect Resting Cytotoxic T Cells", J. Immunol., 147:60-69.
Vajdos et al. (2002) "Comprehensive Functional Maps of the Antigen-binding Site of an Anti-ErbB2 Antibody Obtained with Shotgun Scanning Mutagenesis", J Mol Biol, 320:415-428.
Wu et al. (1987) "Receptor-Mediated in Vitro Gene Transformation by a Soluble DNA Carrier System", J. Biol. Chem., 262:4429-4432.
GenBank accession No. AAD02807.1.
GenBank accession No. AAA43697.1.
GenBank accession No. ABN50712.1.
GenBank accession No. ACA33493.1.
Altschul et al. (1997) "Gapped BLAST and PSI-BLAST: a New Generation of Protein Database Search Programs" Nucleic Acids Res. 25:3389-3402.

* cited by examiner

ANTI-HEMAGGLUTININ ANTIBODIES AND METHODS OF USE THEREOF

RELATED APPLICATIONS

This application claims priority under 35 U.S.C. 119 (e) to U.S. Provisional Patent Application Ser. No. 62/926,914, filed Oct. 28, 2019, and U.S. Provisional Patent Application Ser. No. 63/094,170, filed Oct. 20, 2020, the disclosures of which are hereby incorporated by reference in their entirety.

GOVERNMENT LICENSE RIGHTS

This invention was made with Government support under Agreement HHSO100201700020C, awarded by the U.S. Department of Health and Human Services. The Government has certain rights in the invention.

SEQUENCE LISTING

An official copy of the sequence listing is submitted concurrently with the specification electronically via EFS-Web as an ASCII formatted sequence listing with a file name of "10625US01_SEQ_LIST_ST25.txt", a creation date of Oct. 28, 2020, and a size of about 36 KB. The sequence listing contained in this ASCII formatted document is part of the specification and is herein incorporated by reference in its entirety.

BACKGROUND

Influenza is a highly contagious disease, which has a long history characterized by waves of pandemics, epidemics, resurgences and outbreaks. In spite of annual vaccination efforts, influenza infections result in substantial morbidity and mortality.

Influenza viruses consist of four types: A, B, C, and D. Influenza B causes a significant number of seasonal influenza infections and can be associated with severe influenza, requiring hospitalization.

Hemagglutinin is a trimeric glycoprotein that contains two structural domains, a globular head domain that consists of the receptor-binding site (that is subject to frequent antigenic drift) and the stem region (more conserved among various strains of influenza virus). The HA protein is synthesized as a precursor (HA0), which undergoes proteolytic processing to produce two subunits (HA1 and HA2), which associate with one another to form the stem/globular head structure. The HA1 peptide is responsible for the attachment of virus to the cell surface, and (along with neuraminidase) is required for viral attachment and entry into the host cell. The HA2 peptide forms a stem-like structure that mediates the fusion of viral and cell membranes in endosomes, allowing the release of the ribonucleoprotein complex into the cytoplasm.

New strains of the influenza virus may arise as a result of a phenomenon called antigenic drift, or mutations in the hemagglutinin or neuraminidase molecules which generate new and different epitopes. A consequence of this is that a new vaccine must be produced every year against viruses that are predicted to emerge, a process that is not only costly, but highly inefficient. While technological advances have improved the ability to produce improved influenza antigens for vaccine compositions, there remains a need to provide additional sources of protection against influenza.

SUMMARY

The present disclosure provides antibodies and antigen-binding fragments thereof that bind influenza B HA. The antibodies are useful, inter alia, for inhibiting or neutralizing the activity of influenza B HA.

In a first aspect, the present disclosure provides isolated recombinant monoclonal antibodies or antigen-binding fragments thereof that bind specifically to influenza B hemagglutinin (HA).

In some embodiments, the present disclosure provides an isolated recombinant antibody or antigen-binding fragment thereof that specifically binds to influenza B HA, wherein the antibody has one or more of the following characteristics:

(a) is a fully human monoclonal antibody;
(b) binds to influenza B HA with an $EC_{50}$ of less than about $10^{-10}$ M;
(c) demonstrates an increase in survival in an influenza-infected animal; and/or
(d) comprises (i) three heavy chain complementarity determining regions (CDRs) (HCDR1, HCDR2 and HCDR3) contained within a heavy chain variable region (HCVR) comprising the amino acid sequence set forth in SEQ ID NO: 2; and (ii) three light chain CDRs (LCDR1, LCDR2 and LCDR3) contained within a light chain variable region (LCVR) comprising the amino acid sequence set forth in SEQ ID NO: 10.

In certain embodiments, an antibody, or antigen-binding fragment thereof, provided herein confers an increase in protection from influenza B virus in an animal (e.g., a mammal) when administered either subcutaneously or intravenously and/or when administered prior to infection, or after infection with influenza B virus.

In certain embodiments, an antibody, or antigen-binding fragment thereof, provided herein can alleviate the severity of influenza B infection in an animal (e.g., a mammal) infected with influenza B virus when administered either subcutaneously or intravenously and/or when administered prior to infection, or after infection with influenza B virus.

In certain embodiments, an antibody, or antigen-binding fragment thereof, of the present disclosure provides an increase in protection from influenza B virus, when administered to an animal (e.g., a mammal) exposed to influenza B virus, as a single intravenous dose of about 0.5 mg/kg, about 1.0 mg/kg, about 5 mg/kg, about 10 mg/kg, or about 15 mg/kg body weight of said mammal, starting at 1 day or 2 days or 3 days or 4 days or 5 days or 6 days or 7 days prior to infection, for example, compared to oral administration of an antiviral such as baloxavir marboxil, oseltamivir, zanamivir, or pimodivir.

In some embodiments, an antibody, or antigen-binding fragment thereof, provided herein provides an increase in protection from influenza B virus in an animal (e.g., a mammal), as compared to an isotype (negative) control antibody that has been administered to a comparable animal (e.g., mammal), when administered as a single subcutaneous or intravenous dose ranging from 0.5 mg/kg to about 15 mg/kg body weight of said animal, for example, about 1 mg/kg, about 5 mg/kg, about 7 mg/kg, or about 10 mg/kg, or about 12 mg/kg body weight of said animal.

In some embodiments, an antibody, or antigen-binding fragment thereof, provided herein provides an increase in protection from influenza B when administered to an animal (e.g., a mammal) as a single intravenous dose of about 0.5 mg/kg, about 1.0 mg/kg, about 5 mg/kg, about 10 mg/kg, or about 15 mg/kg body weight of said animal compared to oral administration of an antiviral such as baloxavir, marboxil, oseltamivir, zanamivir, or pimodivir. For example, the antiviral can be oseltamivir administered twice daily for 5 days at a dose of about 2 mg/kg.

In some embodiments, an antibody, or antigen-binding fragment thereof, provided herein confers a survival rate of about 100% in a population of animals (e.g., a mammal) exposed to and infected with influenza B virus, when administered as a single dose of about 0.5 mg/kg, about 1.0 mg/kg, about 5 mg/kg, about 10 mg/kg, or about 15 mg/kg body weight of at 24 hours prior to influenza B exposure and infection.

In some embodiments, an antibody, or antigen-binding fragment thereof, provided herein confers a survival rate of 100% in an animal (e.g., a mammal) infected with influenza virus, when administered as a single intravenous dose of about 0.5 mg/kg, about 1.0 mg/kg, about 5 mg/kg, or about 10 mg/kg, or about 15 mg/kg at 1 day, 2 days, 3 days, 4 days, 5 days, 6 days or 7 days prior to influenza B exposure and/or infection.

In certain embodiments, an antibody, or antigen-binding fragment thereof, demonstrates an increase in protection when administered to an influenza virus infected mammal as a single intravenous dose of about 5 mg/kg to about 15 mg/kg starting at day 1 or day 2 or day 3 post-infection, for example, compared to oral administration of an antiviral such as baloxavir, marboxil, oseltamivir, zanamivir, or pimodivir. For example, the antiviral can be oseltamivir administered twice daily for 5 days at a dose of about 2 mg/kg starting at day 1 or day 2 or day 3 post-infection.

In a related embodiment, an antibody, or antigen-binding fragment thereof, provided herein confers an increase in protection in an animal (e.g., a mammal) infected with influenza virus when administered either subcutaneously or intravenously and/or when administered prior to infection, or after infection with influenza virus.

In some embodiments, an antibody, or antigen-binding fragment thereof, provided herein demonstrates an increase in protection, as compared to an animal administered an isotype (negative) control antibody, when administered to an infected mammal as a single subcutaneous or intravenous dose ranging from 0.5 mg/kg to about 15 mg/kg, for example, about 1 mg/kg, about 5 mg/kg, about 7 mg/kg, or about 10 mg/kg, or about 12 mg/kg.

In some embodiments, an antibody, or antigen-binding fragment thereof, provided herein demonstrates an increase in protection when administered to an influenza virus infected mammal as a single intravenous dose of about 0.5 mg/kg, about 1.0 mg/kg, about 5 mg/kg, about 10 mg/kg, or about 15 mg/kg compared to oral administration of an antiviral such as baloxavir, marboxil, oseltamivir, zanamivir, or pimodivir. For example, the antiviral can be oseltamivir administered twice daily for 5 days at a dose of about 2 mg/kg.

In some embodiments, an antibody, or antigen-binding fragment thereof, provided herein demonstrates a survival rate of about 100% in a population of animals (e.g., mammals) infected with influenza virus, when administered as a single dose of about 0.5 mg/kg, about 1.0 mg/kg, about 5 mg/kg, about 10 mg/kg, or about 15 mg/kg of body weight of the animals at 24 hours or longer post infection.

In some embodiments, an antibody, or antigen-binding fragment thereof, provided herein demonstrates a survival rate of 100% in a population of animals (e.g., mammals) infected with influenza virus, when administered as a single intravenous dose of about 5 mg/kg, or about 10 mg/kg, or about 15 mg/kg of body weight of the animals at 24, 48, 72, or 96 hours post infection.

In some embodiments, an antibody, or antigen-binding fragment thereof, provided herein demonstrates a survival rate of about 100% in a population of animals (e.g., mammals) infected with influenza virus, when administered as a single intravenous dose of about 0.5 mg/kg, about 1.0 mg/kg, about 5 mg/kg, about 10 mg/kg, or about 15 mg/kg of body weight of the animals compared to an 80% survival rate observed in a comparable population of animals with an antiviral such as baloxavir, marboxil, oseltamivir, zanamivir, or pimodivir. For example, the antiviral can be oseltamivir administered orally twice a day for 5 days at a dose of about 2 mg/kg. Survival, as described herein, can be measured at a fixed point after administration of an antibody, or antigen-binding fragment thereof, of the present disclosure (e.g., 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 1 week, 2 weeks, 3 weeks, 4 weeks, 5 weeks, 6 weeks, 7 weeks, 8 weeks, or more, post-administration.

In some embodiments, an antibody, or antigen-binding fragment thereof, of the present disclosure provides an additive protective effect in an animal (e.g., a mammal) infected with influenza virus when administered with an antiviral such as baloxavir, marboxil, oseltamivir, zanamivir, or pimodivir. For example, the antiviral can be oseltamivir administered at greater than 48 hours post infection.

In some embodiments, an antibody, or antigen-binding fragment thereof, of the present disclosure provides an additive protective effect in an animal (e.g., a mammal) infected with influenza virus when administered with an antiviral such as baloxavir, marboxil, oseltamivir, zanamivir, or pimodivir. For example, the antiviral can be oseltamivir administered at 72 hours post infection.

In some embodiments, an antibody, or antigen-binding fragment thereof, of the present disclosure provides an additive protective effect when used in combination with an antiviral when the antibody is administered to an influenza virus infected animal (e.g., mammal) as a single intravenous dose ranging from about 7 mg/kg to about 15 mg/kg body weight of the animal and the antiviral such as baloxavir, marboxil, oseltamivir, zanamivir, or pimodivir is administered orally twice daily for 5 days at a dose of about 2 mg/kg body weight of the animal.

In some embodiments, an antibody, or antigen-binding fragment thereof, of the present disclosure provides an additive protective effect when used in combination with an antiviral such as baloxavir, marboxil, oseltamivir, zanamivir, or pimodivir at 96 hours after influenza virus infection, wherein the antibody is administered to an animal as a single intravenous dose ranging from about 7 mg/kg to about 15 mg/kg body weight of the animal and the antiviral, for example, oseltamivir, zanamivir, or pimodivir, is administered orally twice daily for 5 days at a dose of about 2 mg/kg body weight of the animal.

In some embodiments, an antibody, or antigen-binding fragment thereof, provided herein may be administered intravenously, intranasally, subcutaneously, intradermally, or intramuscularly and the antiviral may be administered orally or intravenously.

In some embodiments, the antiviral is administered prior to, concurrently with, or after administration of an antibody provided herein.

In some embodiments, the antibody, or antigen-binding fragment thereof, and/or the antiviral such as baloxavir, marboxil, oseltamivir, zanamivir, or pimodivir may be administered as a single dose, or as multiple doses.

An exemplary anti-influenza B HA antibody is provided in Tables 1 and 2 herein. Table 1 sets forth the amino acid sequence identifiers of the heavy chain variable region (HCVR), light chain variable region (LCVR), heavy chain complementarity determining regions (HCDR1, HCDR2, and HCDR3), light chain complementarity determining regions (LCDR1, LCDR2, and LCDR3), heavy chain (HC), and light chain (LC) of an exemplary anti-influenza B HA antibody. Table 2 sets forth the nucleic acid sequence identifiers of the HCVR, LCVR, HCDR1, HCDR2, HCDR3, LCDR1, LCDR2, LCDR3, HC, and LC of the exemplary anti-influenza B HA antibody.

Provided herein are antibodies, or antigen-binding fragments thereof, comprising an HCVR comprising an amino acid sequence according to Table 1, or a substantially similar sequence thereof having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity thereto.

In some embodiments, the antibodies, or antigen-binding fragments thereof, which specifically bind influenza B HA, comprise an HCVR amino acid sequence of SEQ ID NO: 2.

Provided herein are antibodies, or antigen-binding fragments thereof, comprising an LCVR comprising an amino acid sequence according to Table 1, or a substantially similar sequence thereof having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity thereto.

In some embodiments, the antibodies, or antigen-binding fragments thereof, which specifically bind influenza B HA, comprise an LCVR amino acid sequence of SEQ ID NO: 10.

In some embodiments, the isolated antibody or antigen-binding fragment that specifically binds influenza B HA comprises an HCVR/LCVR amino acid sequence pair of SEQ ID NOs: 2/10.

In some embodiments, the isolated antibody or antigen-binding fragment comprises:
(a) an HCDR1 domain having an amino acid sequence of SEQ ID NO: 4;
(b) an HCDR2 domain having an amino acid sequence of SEQ ID NO: 6;
(c) an HCDR3 domain having an amino acid sequence of SEQ ID NO: 8;
(d) an LCDR1 domain having an amino acid sequence of SEQ ID NO: 12;
(e) an LCDR2 domain having an amino acid sequence of SEQ ID NO: 14; and
(f) an LCDR3 domain having an amino acid sequence of SEQ ID NO: 16.

In some embodiments, the isolated antibody or antigen-binding fragment, which specifically binds influenza B HA, comprises (a) an HCDR1 of SEQ ID NO: 4, (b) an HCDR2 of SEQ ID NO: 6; (c) an HCDR3 of SEQ ID NO: 8; (d) an LCDR1 of SEQ ID NO: 12; (e) an LCDR2 of SEQ ID NO: 14 and (f) an LCDR3 of SEQ ID NO: 16.

In some embodiments, the isolated antibody or antigen-binding fragment, which specifically binds influenza B HA, comprises (a) an HCDR3 of SEQ ID NO: 8 and (b) an LCDR3 of SEQ ID NO: 16.

The present disclosure also provides antibodies, or antigen-binding fragments thereof, comprising a heavy chain CDR1 (HCDR1) comprising an amino acid sequence of SEQ ID NO: 4, or a substantially similar sequence thereof having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity thereto.

The present disclosure also provides antibodies, or antigen-binding fragments thereof, comprising a heavy chain CDR2 (HCDR2) comprising an amino acid sequence of SEQ ID NO: 6, or a substantially similar sequence thereof having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity thereto.

The present disclosure also provides antibodies, or antigen-binding fragments thereof, comprising a heavy chain CDR3 (HCDR3) comprising an amino acid sequence of SEQ ID NO: 8, or a substantially similar sequence thereof having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity thereto.

The present disclosure also provides antibodies, or antigen-binding fragments thereof, comprising a light chain CDR1 (LCDR1) comprising an amino acid sequence of SEQ ID NO: 12, or a substantially similar sequence thereof having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity thereto.

The present disclosure also provides antibodies, or antigen-binding fragments thereof, comprising a light chain CDR2 (LCDR2) comprising an amino acid sequence of SEQ ID NO: 14, or a substantially similar sequence thereof having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity thereto.

The present disclosure also provides antibodies, or antigen-binding fragments thereof, comprising a light chain CDR3 (LCDR3) comprising an amino acid sequence of SEQ ID NO: 16, or a substantially similar sequence thereof having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity thereto.

The present disclosure also provides antibodies, or antigen-binding fragments thereof, comprising an HCDR3 and an LCDR3 amino acid sequence pair (HCDR3/LCDR3) comprising SEQ ID NOs: 8/16, or a substantially similar sequence thereof having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity thereto.

The present disclosure also provides antibodies, or antigen-binding fragments thereof, comprising a set of six CDRs (i.e., HCDR1-HCDR2-HCDR3-LCDR1-LCDR2-LCDR3) contained within HCVR/LCVR amino acid sequence of the exemplary anti-influenza B HA antibody shown in Table 1. In certain embodiments, the HCDR1-HCDR2-HCDR3-LCDR1-LCDR2-LCDR3 amino acid sequence set comprises SEQ ID NOs: 4-6-8-12-14-16.

Methods and techniques for identifying CDRs within HCVR and LCVR amino acid sequences are well known in the art and can be used to identify CDRs within the specified HCVR and/or LCVR amino acid sequences disclosed herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest," National Institutes of Health, Bethesda, Md. (1991); Al-Lazikani et al., *J. Mol. Biol.* 273:927-948 (1997); and Martin et al., *Proc. Natl. Acad. Sci. USA* 86:9268-9272 (1989). Public databases are also available for identifying CDR sequences within an antibody.

Also provided herein are antibodies and antigen-binding fragments thereof that compete for specific binding to influenza B HA with an antibody or antigen-binding fragment thereof comprising the CDRs of an HCVR and the CDRs of an LCVR, wherein the HCVR and LCVR each has an amino acid sequence according to the HCVR and LCVR sequences listed in Table 1.

The present disclosure also provides antibodies and antigen-binding fragments thereof that cross-compete for binding to influenza B HA, or that bind the same epitope on influenza B HA, as a reference antibody or antigen-binding fragment thereof comprising the CDRs of an HCVR and the CDRs of an LCVR, wherein the HCVR and LCVR each has an amino acid sequence according to the HCVR and LCVR sequences listed in Table 1.

The present disclosure also provides isolated antibodies and antigen-binding fragments thereof that block influenza B HA attachment to, and/or entry into a host cell.

In certain embodiments, the antibodies or antigen-binding fragments are bispecific comprising a first binding specificity to a first epitope in the influenza B HA and a second binding specificity to another antigen.

In a second aspect, provided herein are nucleic acid molecules (e.g., DNA or RNA molecules) encoding anti-influenza B HA antibodies or portions thereof. For example, the nucleic acid molecules encoding the HCVR amino acid sequences are listed in Table 2; in certain embodiments the nucleic acid molecule comprises an HCVR polynucleotide sequence of SEQ ID NO: 1, or a substantially similar sequence thereof having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity thereto. The nucleic acid molecules encoding the LCVR amino acid sequences are also listed in Table 2; in certain embodiments the nucleic acid molecule comprises an LCVR polynucleotide sequence of SEQ ID NO: 9, or a substantially similar sequence thereof having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity thereto.

Also provided herein are nucleic acid molecules encoding the HCDR1 amino acid sequence listed in Table 1; in certain embodiments the nucleic acid molecule comprises the HCDR1 nucleic acid sequence listed in Table 2, or a substantially similar sequence thereof having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity thereto.

Also provided herein are nucleic acid molecules encoding the HCDR2 amino acid sequence listed in Table 1; in certain embodiments the nucleic acid molecule comprises the HCDR2 nucleic acid sequence listed in Table 2, or a substantially similar sequence thereof having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity thereto.

Also provided herein are nucleic acid molecules encoding the HCDR3 amino acid sequence listed in Table 1; in certain embodiments the nucleic acid molecule comprises the HCDR3 nucleic acid sequence listed in Table 2, or a substantially similar sequence thereof having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity thereto.

Also provided herein are nucleic acid molecules encoding the LCDR1 amino acid sequence listed in Table 1; in certain embodiments the nucleic acid molecule comprises the LCDR1 nucleic acid sequence listed in Table 2, or a substantially similar sequence thereof having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity thereto.

Also provided herein are nucleic acid molecules encoding the LCDR2 amino acid sequence listed in Table 1; in certain embodiments the nucleic acid molecule comprises the LCDR2 nucleic acid sequence listed in Table 2, or a substantially similar sequence thereof having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity thereto.

Also provided herein are nucleic acid molecules encoding the LCDR3 amino acid sequence listed in Table 1; in certain embodiments the nucleic acid molecule comprises the LCDR3 nucleic acid sequence listed in Table 2, or a substantially similar sequence thereof having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity thereto.

Also provided herein are nucleic acid molecules encoding an HCVR, wherein the HCVR comprises a set of three CDRs (i.e., HCDR1-HCDR2-HCDR3), wherein the HCDR1-HCDR2-HCDR3 amino acid sequence set is as defined by the exemplary anti-influenza HA antibody listed in Table 1.

Also provided herein are nucleic acid molecules encoding an LCVR, wherein the LCVR comprises a set of three CDRs (i.e., LCDR1-LCDR2-LCDR3), wherein the LCDR1-LCDR2-LCDR3 amino acid sequence set is as defined by the exemplary anti-influenza HA antibody listed in Table 1.

Also provided herein are nucleic acid molecules encoding both an HCVR and an LCVR, wherein the HCVR comprises an amino acid sequence of SEQ ID NO: 2 and wherein the LCVR comprises an amino acid sequence of SEQ ID NO: 10. In certain embodiments, the nucleic acid molecule comprises an HCVR or LCVR polynucleotide sequence listed in Table 2, or a substantially similar sequence thereof having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity thereto. In certain embodiments, the nucleic acid molecule encodes an HCVR and LCVR, wherein the HCVR and LCVR are both derived from the same anti-influenza B HA antibody listed in Table 1.

Also provided are nucleic acid molecules encoding any of the heavy chain amino acid sequences and/or any of the light chain amino acid sequences listed in Table 1.

In a related aspect, provided herein are recombinant expression vectors capable of expressing a polypeptide comprising a heavy or light chain variable region of an anti-influenza B HA antibody. For example, the vectors can include recombinant expression vectors comprising any of the nucleic acid molecules mentioned above, i.e., nucleic acid molecules encoding any of the HCVR, LCVR, and/or CDR sequences as set forth in Table 1. Also included within the scope of the present disclosure are host cells into which such vectors have been introduced, as well as methods of producing the antibodies or portions thereof by culturing the host cells under conditions permitting production of the antibodies or antibody fragments, and recovering the antibodies and antibody fragments so produced.

In a third aspect, provided herein is a pharmaceutical composition comprising a therapeutically effective amount of at least one recombinant monoclonal antibody or antigen-binding fragment thereof which specifically binds influenza B HA and a pharmaceutically acceptable carrier. In a related aspect, the composition can be a combination of an anti-influenza B HA antibody and a second therapeutic agent. In some embodiments, the second therapeutic agent is any agent that is advantageously combined with an anti-influenza B HA antibody. Exemplary agents that may be advantageously combined with an anti-influenza B HA antibody include, without limitation, other agents that bind and/or inhibit influenza HA activity (including other antibodies or antigen-binding fragments thereof, such as an antibody that binds and/or inhibits influenza A HA, etc.) and/or agents, which do not directly bind influenza HA but nonetheless inhibit viral activity including infectivity of host cells. In certain embodiments, the pharmaceutical composition comprises: (a) a first anti-influenza B HA antibody or antigen-binding fragment thereof; (b) a second anti-influenza B HA antibody or antigen-binding fragment thereof, wherein the first antibody binds to a first epitope on influenza B HA and the second antibody binds to a second epitope on influenza B HA wherein the first and second epitopes are distinct and non-overlapping; and (c) a pharmaceutically acceptable carrier or diluent. In certain embodiments, the pharmaceutical composition comprises: (a) a first anti-influenza B HA antibody or antigen-binding fragment thereof; (b) a second anti-influenza B HA antibody or antigen-binding fragment thereof, wherein the first antibody does not cross-compete with the second antibody for binding to influenza B HA; and (c) a pharmaceutically acceptable carrier or diluent. In certain embodiments, the pharmaceutical composition comprises: (a) a first anti-influenza B HA antibody or antigen-binding fragment thereof; (b) a second anti-influenza antibody or antigen-binding fragment thereof, which interacts with a different influenza antigen, wherein the first antibody binds to an epitope on influenza B HA and the second antibody binds to an epitope on a different influenza antigen; and (c) a pharmaceutically acceptable carrier or diluent. In certain embodiments, the pharmaceutical composition comprises: (a) a first anti-influenza B HA antibody or antigen-binding fragment thereof; (b) a second antibody or antigen-binding fragment thereof, which interacts with a different viral (non-influenza) antigen, wherein the first antibody binds to an epitope on influenza B HA and the second antibody binds to an epitope on a different viral (non-influenza) antigen; and (c) a pharmaceutically acceptable carrier or diluent. Additional combination therapies and co-formulations involving the anti-influenza B HA antibodies provided herein are disclosed elsewhere herein. In certain embodiments, the pharmaceutical composition comprises: (a) an anti-influenza B HA antibody or antigen-binding fragment thereof, and (b) an anti-influenza A HA antibody or antigen-binding fragment thereof.

In a fourth aspect, provided herein are therapeutic methods for treating a disease or disorder associated with influenza B HA (such as viral infection in a subject), or at least one symptom associated with the viral infection, using an anti-influenza B HA antibody or antigen-binding portion of an antibody provided herein, wherein the therapeutic methods comprise administering a therapeutically effective amount of a pharmaceutical composition comprising an antibody or antigen-binding fragment of an antibody to the subject in need thereof. The disorder treated is any disease or condition, which is improved, ameliorated, inhibited or prevented by inhibition of influenza HA activity. In certain embodiments, the disclosure provides methods to prevent, treat or ameliorate at least one symptom of influenza B infection, the method comprising administering a therapeutically effective amount of an anti-influenza HA antibody or antigen-binding fragment thereof to a subject in need thereof.

In some embodiments, the present disclosure provides methods to ameliorate, alleviate, or reduce the severity, duration, or frequency of occurrence, of at least one symptom of influenza infection in a subject by administering an anti-influenza B HA antibody provided herein, wherein the at least one symptom is selected from the group consisting of headache, fever, aches, rhinorrhea (nasal congestion), chills, fatigue, weakness, sore throat, cough, shortness of breath, vomiting, diarrhea, pneumonia, bronchitis, and death.

In certain embodiments, provided herein are methods to decrease viral load in a subject, the methods comprising administering to the subject an effective amount of an antibody or fragment thereof that binds influenza B HA and blocks influenza virus binding and/or entry into the host cell.

In certain embodiments, the antibody or antigen-binding fragment thereof may be administered prophylactically or therapeutically to a subject having, or at risk of having, or predisposed to developing an influenza infection. The subjects at risk include, but are not limited to, an immunocompromised person, for example, a person who is immunocompromised because of autoimmune disease, or those persons receiving immunosuppressive therapy (for example, following organ transplant), or those persons afflicted with human immunodeficiency syndrome (HIV) or acquired immune deficiency syndrome (AIDS), certain forms of anemia that deplete or destroy white blood cells, those persons receiving radiation or chemotherapy, or those persons afflicted with an inflammatory disorder. Other subjects at risk for acquiring an influenza infection include an elderly adult (65 years of age or older), children younger than 2 years of age, healthcare workers, and people with underlying medical conditions such as pulmonary infection, heart disease or diabetes. Also, any person who comes into physical contact or close physical proximity with an infected individual has an increased risk of developing an influenza virus infection. Moreover, a subject is at risk of contracting an influenza infection due to proximity to an outbreak of the disease, e.g. subject resides in a densely-populated city or in close proximity to subjects having confirmed or suspected infections of influenza virus, or choice of employment, e.g. hospital worker, pharmaceutical researcher, traveler to infected area, or frequent flier.

In certain embodiments, the antibody or antigen-binding fragment thereof is administered in combination with a second therapeutic agent to the subject in need thereof. The second therapeutic agent may be selected from the group consisting of an anti-inflammatory drug (such as corticosteroids, and non-steroidal anti-inflammatory drugs), an anti-infective drug, a different antibody to influenza HA (e.g., an antibody to influenza A HA), an antibody to a different influenza antigen (e.g. neuraminidase), an anti-viral drug, a decongestant, an anti-histamine, a vaccine for influenza, a dietary supplement such as anti-oxidants and any other drug or therapy known in the art useful for ameliorating at least one symptom of the influenza infection, or for reducing the viral load in a patient. In certain embodiments, the second therapeutic agent may be an agent that helps to counteract or reduce any possible side effect(s) associated with an antibody or antigen-binding fragment thereof provided herein, if such side effect(s) should occur. The antibody or fragment thereof may be administered subcutaneously, intravenously, intradermally, intraperitoneally, orally, intranasally, intramuscularly, or intracranially. In some embodiments, the antibody may be administered as a single intravenous infusion for maximum concentration of the antibody in the serum of the subject. The antibody or fragment thereof may be administered at a dose of about 0.01 mg/kg of body weight to about 100 mg/kg of body weight of the subject. In certain embodiments, an antibody disclosed herein may be administered at one or more doses comprising between 50 mg to 5000 mg.

In a fifth aspect, provided herein is an isolated recombinant antibody or antigen-binding fragment thereof that specifically binds to influenza B hemagglutinin (HA), wherein the antibody has one or more of the following characteristics: (a) binds to influenza B HA with an $EC_{50}$ of less than about $10^{-9}M$; (b) demonstrates an increase in survival in an influenza B-infected animal after administration to said influenza B-infected animal, as compared to a comparable influenza B-infected animal without said administration; and/or (c) comprises (i) three heavy chain complementarity determining regions (CDRs) (HCDR1, HCDR2, and HCDR3) contained within a heavy chain variable region (HCVR) comprising the amino acid sequence having at least about 90% sequence identity to the HCVR set forth in SEQ ID NO: 2; and (ii) three light chain CDRs (LCDR1, LCDR2, and LCDR3) contained within a light chain variable region (LCVR) comprising the amino acid sequence having at least about 90% sequence identity to the LCVR set forth in SEQ ID NO: 10.

In some embodiments, when prophylactically administered to a mammal as a single intravenous dose of about 5 mg/kg body weight of the mammal or about 0.5 mg/kg, the isolated antibody or antigen-binding fragment thereof protects the mammal from infection by subsequent exposure to influenza B virus. In some embodiments, when prophylactically administered to a mammal prior to exposure to influenza B virus, the isolated antibody or antigen-binding fragment thereof decreases the risk of influenza infection in the mammal. In some embodiments, when the isolated antibody or antigen-binding fragment thereof is administered to a mammal, the isolated antibody or antigen-binding fragment thereof ameliorates, alleviates, or reduces the severity, duration, or frequency of occurrence of at least one symptom of influenza infection in said mammal. In some embodiments, the at least one symptom is selected from the group consisting of headache, fever, aches, rhinorrhea (nasal congestion), chills, fatigue, weakness, sore throat, cough, shortness of breath, vomiting, diarrhea, pneumonia, bronchitis, and death.

In some embodiments, when the isolated antibody or antigen-binding fragment thereof is administered to each of a plurality of mammals as a single prophylactic dose of about 0.5 mg/kg, said plurality of mammals has a survival rate of at least about 80% at 19 days post-administration. In some embodiments, when the isolated antibody or antigen-binding fragment thereof is administered to each of a plurality of mammals as a single prophylactic dose of about 0.5 mg/kg, said plurality of mammals has a survival rate of at least about 90% at 19 days post-administration. In some embodiments, when the isolated antibody or antigen-binding fragment thereof is administered to each of a plurality of mammals as a single prophylactic dose of about 0.5 mg/kg, said plurality of mammals has a survival rate of about 100% at 19 days post-administration. In some embodiments, when the isolated antibody or antigen-binding fragment thereof is administered to each of a plurality of mammals as a single prophylactic dose of about 5.0 mg/kg, said plurality of mammals has a survival rate of about 80% at 19 days post-administration. In some embodiments, when the isolated antibody or antigen-binding fragment thereof is administered to each of a plurality of mammals as a single prophylactic dose of about 5.0 mg/kg, said plurality of mammals has a survival rate of about 90% at 19 days post-administration. In some embodiments, when the isolated antibody or antigen-binding fragment thereof is administered to each of a plurality of mammals as a single prophylactic dose of about 5.0 mg/kg, said plurality of mammals has a survival rate of about 100% at 19 days post-administration. In some embodiments, the survival rate is apparent at 13 days post administration.

In some embodiments, the present disclosure provides an isolated antibody or antigen-binding fragment thereof as described above, comprising an HCVR having an amino acid sequence of SEQ ID NO: 2. In some embodiments, the isolated antibody or antigen-binding fragment thereof comprises an LCVR having an amino acid sequence of SEQ ID NO: 10.

In a sixth aspect, provided herein is an isolated antibody or antigen-binding fragment thereof, comprising: (a) an HCDR1 domain having an amino acid sequence of SEQ ID NO: 4; (b) an HCDR2 domain having an amino acid sequence of SEQ ID NO: 6; (c) an HCDR3 domain having an amino acid sequence of SEQ ID NO: 8; (d) an LCDR1 domain having an amino acid sequence of SEQ ID NO: 12; (e) an LCDR2 domain having an amino acid sequence of SEQ ID NO: 14; and (f) an LCDR3 domain having an amino acid sequence of SEQ ID NO: 16.

In some embodiments, the isolated antibody or antigen-binding fragment thereof specifically binds to influenza B hemagglutinin (HA). In some embodiments, when the isolated antibody or antigen-binding fragment thereof is prophylactically administered to a mammal as a single intravenous dose of about 5 mg/kg body weight of the mammal or about 0.5 mg/kg, protects the mammal from infection by subsequent exposure to influenza B virus. In some embodiments, when the isolated antibody or antigen-binding fragment thereof is prophylactically administered to a mammal prior to exposure to influenza B virus, decreases the risk of influenza infection in the mammal. In some embodiments, when the isolated antibody or antigen-binding fragment thereof is administered to a mammal, said isolated antibody or antigen-binding fragment thereof ameliorates, alleviates, or reduces the severity, duration, or frequency of occurrence of at least one symptom of influenza infection in said mammal. In some embodiments, the at least one symptom is selected from the group consisting of headache, fever, aches, rhinorrhea (nasal congestion), chills, fatigue, weakness, sore throat, cough, shortness of breath, vomiting, diarrhea, pneumonia, bronchitis, and death.

In some embodiments, when the isolated antibody or antigen-binding fragment thereof is administered to each of a plurality of mammals as a single prophylactic dose of about 0.5 mg/kg, said plurality of mammals has a survival rate of at least about 80% at 19 days post-administration. In some embodiments, when the isolated antibody or antigen-binding fragment thereof is administered to each of a plurality of mammals as a single prophylactic dose of about 0.5 mg/kg, said plurality of mammals has a survival rate of at least about 90% at 19 days post-administration. In some embodiments, when the isolated antibody or antigen-binding fragment thereof is administered to each of a plurality of mammals as a single prophylactic dose of about 0.5 mg/kg, said plurality of mammals has a survival rate of about 100% at 19 days post-administration. In some embodiments, when the isolated antibody or antigen-binding fragment thereof is administered to each of a plurality of mammals as a single prophylactic dose of about 5.0 mg/kg, said plurality of mammals has a survival rate of about 80% at 19 days post-administration. In some embodiments, when the isolated antibody or antigen-binding fragment thereof is administered to each of a plurality of mammals as a single prophylactic dose of about 5.0 mg/kg, said plurality of mammals has a survival rate of about 90% at 19 days post-administration. In some embodiments, when the isolated antibody or antigen-binding fragment thereof is administered to each of a plurality of mammals as a single prophylactic dose of about 5.0 mg/kg, said plurality of mammals has a survival rate of about 100% at 19 days post-administration. In some embodiments, the survival rate is apparent at 13 days post administration.

In some embodiments, the isolated antibody or antigen-binding fragment thereof described above comprises an HCVR having an amino acid sequence of SEQ ID NO: 2. In some embodiments, the isolated antibody or antigen-binding fragment thereof comprises an LCVR having an amino acid sequence of SEQ ID NO: 10. In some embodiments, the isolated antibody or antigen-binding fragment thereof comprises an HCVR/LCVR amino acid sequence pair of SEQ ID NOs: 2/10. In some embodiments, the isolated antibody or antigen-binding fragment thereof is an IgG1 antibody. In some embodiments, the isolated antibody or antigen-binding fragment thereof is an IgG4 antibody. In some embodiments, the isolated antibody or antigen-binding fragment thereof is a bispecific antibody.

In a seventh aspect, provided herein is a pharmaceutical composition comprising the isolated antibody or antigen-binding fragment thereof described above and a pharmaceutically acceptable carrier or diluent.

In some embodiments, the pharmaceutical composition further comprises a second therapeutic agent. In some embodiments, the second therapeutic agent is selected from the group consisting of: an anti-viral drug, an anti-inflammatory drug, a different antibody that binds specifically to influenza HA, a vaccine for influenza, a dietary supplement, and another palliative therapy to treat an influenza infection. In some embodiments, the anti-inflammatory drug is selected from the group consisting of corticosteroids and non-steroidal anti-inflammatory drugs. In some embodiments, the dietary supplement is an anti-oxidant. In some embodiments, the anti-viral drug is oseltamivir. In some embodiments, the anti-viral drug is an anti-influenza A drug. In some embodiments, the anti-influenza A drug is an antibody. In some embodiments, the antibody binds specifically to influenza A HA.

In some embodiments, the present disclosure provides a polynucleotide molecule comprising a polynucleotide sequence that encodes an HCVR or an LCVR of an antibody as described above. In some embodiments, the present disclosure provides a vector comprising that polynucleotide. In some embodiments, the present disclosure provides a cell comprising that vector.

In an eighth aspect, provided herein is a method of preventing, treating, or ameliorating at least one symptom of influenza infection in a subject infected with influenza, the method comprising administering an antibody or antigen-binding fragment as described above, or a pharmaceutical composition as described above, to said subject.

In some embodiments, the at least one symptom is selected from the group consisting of fever, cough, body aches, rhinorrhea, shortness of breath, pneumonia and bronchitis. In some embodiments, the pharmaceutical composition is administered prophylactically to said subject. In some embodiments, the subject is selected from the group consisting of: an immunocompromised individual, an adult 65 years of age or older, a healthcare worker, and a person with a history of medical problems or an underlying medical condition. In some embodiments, the underlying medical condition is selected from the group consisting of: a heart problem and diabetes. In some embodiments, the pharmaceutical composition is administered in combination with a second therapeutic agent. In some embodiments, the second therapeutic agent is selected from the group consisting of: an anti-viral drug, an anti-inflammatory drug, a different antibody that binds specifically to influenza HA, a vaccine for influenza, a dietary supplement, and another palliative therapy to treat an influenza infection. In some embodiments, the anti-inflammatory drug is selected from the group consisting of corticosteroids and non-steroidal anti-inflammatory drugs. In some embodiments, the dietary supplement is an anti-oxidant. In some embodiments, the second therapeutic agent is administered via a different route of administration as said antibody or antigen-binding fragment thereof. In some embodiments, the second therapeutic agent is administered orally. In some embodiments, the anti-viral drug is oseltamivir. In some embodiments, the oseltamivir is administered prior to administration of said antibody or antigen-binding fragment thereof. In some embodiments, the oseltamivir is administered concurrently with said antibody or antigen-binding fragment thereof. In some embodiments, the oseltamivir is administered after administration of said antibody or antigen-binding fragment thereof. In some embodiments, the anti-viral drug is an anti-influenza A drug. In some embodiments, the anti-influenza A drug is an antibody. In some embodiments, the antibody binds specifically to influenza A HA. In some embodiments, the pharmaceutical composition is administered subcutaneously, intravenously, intradermally, intramuscularly, intranasally, or orally.

The present disclosure also includes use of an anti-influenza B HA antibody or antigen-binding fragment thereof for treating a disease or disorder that would benefit from the blockade of influenza HA binding and/or activity. The present disclosure also includes use of an anti-influenza B HA antibody or antigen-binding fragment thereof in the manufacture of a medicament for the treatment of a disease or disorder that would benefit from the blockade of influenza HA binding and/or activity.

Other embodiments will become apparent from a review of the ensuing detailed description.

DETAILED DESCRIPTION

Before the present methods are described, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present disclosure, preferred methods and materials are now described. All publications mentioned herein are incorporated herein by reference in their entirety.

The present disclosure provides antibodies and antigen-binding fragments thereof that bind influenza B HA. The antibodies are useful, inter alia, for inhibiting or neutralizing the activity of influenza B HA.

The antibodies provided herein can be full-length (for example, an IgG1 or IgG4 full-length antibody) or may comprise only an antigen-binding portion (for example, a Fab, F(ab')$_2$ or scFv fragment), and may be modified to affect functionality, e.g., to increase persistence in the host or to increase effector function or eliminate residual effector functions (Reddy et al., 2000, J. Immunol. 164:1925-1933), relative to an unmodified antibody. In certain embodiments, the antibodies may be bispecific.

In some embodiments, the antibodies are useful for blocking attachment of the influenza virus to the host cell and/or for preventing the entry of the influenza virus into host cells. In some embodiments, the antibodies function by inhibiting the cell-to-cell transmission of the virus. In certain embodiments, the antibodies are useful in preventing, treating or ameliorating at least one symptom of influenza virus infection in a subject. In certain embodiments, the antibodies may be administered prophylactically or therapeutically to a subject having, or at risk of acquiring, an influenza virus infection. In certain embodiments, compositions containing at least one antibody provided herein may be administered to a subject for whom a vaccine is contra-indicated, or for whom a vaccine is less efficacious, for example, an elderly patient, a very young patient, a patient who may be allergic to any one or more components of a vaccine, or an immunocompromised patient who may be non-responsive to the immunogens in a vaccine. In certain embodiments, compositions containing at least one antibody provided herein may be administered to medical staff, hospitalized patients or nursing home residents or other high-risk patients during an influenza outbreak. In certain embodiments, compositions containing at least one antibody provided herein may be administered as a first line treatment to patients in the event that a predicted yearly vaccine is ineffective, or in the event of a pandemic with a strain that has undergone a major antigenic shift.

Definitions

The term "influenza hemagglutinin," also called "influenza HA," is a trimeric glycoprotein found on the surface of influenza virions, which mediates viral attachment (via HA1 binding to α-2,3- or α-2,6-sialic acids) and entry (through conformational change) into host cells. The HA is comprised of two structural domains: a globular head domain containing the receptor binding site (subject to high frequency of antigenic mutations) and the stem region (more conserved among various strains of influenza virus). The influenza HA is synthesized as a precursor (HA0) that undergoes proteolytic processing to produce two subunits (HA1 and HA2), which associate with one another to form the stem/globular head structure. The viral HA is the most variable antigen on the virus (18 subtypes can be classified into two groups), but the stem (HA2) is highly conserved within each group. The amino acid sequence of full-length Influenza B HA is exemplified by the HA from B/Victoria/2/87, SEQ ID NO: 21 (GenBank accession number AAA43697.1), the HA from B/Nanchang/3451/93, SEQ ID NO: 22 (partial sequence; GenBank accession number AAD02807.1), the HA from B/Singapore/11/1994, SEQ ID NO: 23 (GenBank accession number ABN50712.1), and the HA from B/Florida/4/2006, SEQ ID NO: 24 (Gen Bank accession number ACA33493.1). The term "influenza-HA" also includes protein variants of influenza HA isolated from other influenza B isolates, as well as from influenza A isolates. The term "influenza-HA" also includes recombinant influenza HA or a fragment thereof. The term also encompasses influenza HA or a fragment thereof coupled to, for example, histidine tag, mouse or human Fc, or a signal sequence.

The term "influenza infection", as used herein, also characterized as "flu" refers to the severe acute respiratory illness caused by influenza virus. The term includes respiratory tract infection and the symptoms that include high fever, headache, general aches and pains, fatigue and weakness, in some instances extreme exhaustion, stuffy nose, sneezing, sore throat, chest discomfort, cough, shortness of breath, bronchitis, pneumonia and death in severe cases.

The term "surface plasmon resonance", refers to an optical phenomenon that allows for the analysis of real-time biomolecular interactions by detection of alterations in protein concentrations within a biosensor matrix, for example using the BIACORE™ system (Pharmacia Biosensor AB, Uppsala, Sweden and Piscataway, N.J.

Bio-layer interferometry is a label-free technology for measuring biomolecular interactions. It is an optical analytical technique that analyzes the interference pattern of white light reflected from two surfaces: a layer of immobilized protein on the biosensor tip, and an internal reference layer. Any change in the number of molecules bound to the biosensor tip causes a shift in the interference pattern that can be measured in real-time (Abdiche, Y. N., et al. Analytical Biochemistry, (2008), 377(2), 209-217). In certain embodiments, a "real-time bio-layer interferometer based biosensor (Octet HTX assay)" was used to assess the binding characteristics of certain of the anti-influenza HA antibodies.

The term "epitope" refers to an antigenic determinant that interacts with a specific antigen-binding site in the variable region of an antibody molecule known as a paratope. A single antigen may have more than one epitope. Thus, different antibodies may bind to different areas on an antigen and may have different biological effects. The term "epitope" also refers to a site on an antigen to which B and/or T cells respond. It also refers to a region of an antigen that is bound by an antibody. Epitopes may be defined as structural or functional. Functional epitopes are generally a subset of the structural epitopes and have those residues that directly contribute to the affinity of the interaction. Epitopes may also be conformational, that is, composed of non-linear amino acids. In certain embodiments, epitopes may include determinants that are chemically active surface groupings of molecules such as amino acids, sugar side chains, phosphoryl groups, or sulfonyl groups, and, in certain embodiments, may have specific three-dimensional structural characteristics, and/or specific charge characteristics.

The term "cross-competes", as used herein, means an antibody or antigen-binding fragment thereof binds to an antigen and inhibits or blocks the binding of another antibody or antigen-binding fragment thereof. The term also includes competition between two antibodies in both orientations, i.e., a first antibody that binds and blocks binding of second antibody and vice-versa. In certain embodiments, the first antibody and second antibody may bind to the same epitope. Alternatively, the first and second antibodies may bind to different, but overlapping epitopes such that binding of one inhibits or blocks the binding of the second antibody, e.g., via steric hindrance. Cross-competition between antibodies may be measured by methods known in the art, for example, by a real-time, label-free bio-layer interferometry assay. To determine if a test antibody cross-competes with a reference anti-influenza B antibody, the reference antibody is allowed to bind to an influenza virus HA or peptide under saturating conditions. Next, the ability of a test antibody to bind to the influenza virus HA is assessed. If the test antibody is able to bind to influenza virus HA following saturation binding with the reference anti-influenza virus HA antibody, it can be concluded that the test antibody binds to a different epitope than the reference anti-influenza virus HA antibody. On the other hand, if the test antibody is not able to bind to the influenza virus HA following saturation binding with the reference anti-influenza virus HA antibody, then the test antibody may bind to the same epitope as the epitope bound by the reference anti-influenza virus HA antibody.

By the phrase "therapeutically effective amount" is meant an amount that produces the desired effect for which it is administered. The exact amount will depend on the purpose of the treatment, and will be ascertainable by one skilled in the art using known techniques (see, for example, Lloyd (1999) The Art, Science and Technology of Pharmaceutical Compounding).

As used herein, the term "subject" refers to an animal, for example a mammal, such as a human, in need of amelioration, prevention and/or treatment of a disease or disorder such as viral infection. The subject may have an influenza infection or is predisposed to developing an influenza virus infection. Subjects "predisposed to developing an influenza virus infection", or subjects "who may be at elevated risk for contracting an influenza virus infection", are those subjects with compromised immune systems because of autoimmune disease, those persons receiving immunosuppressive therapy (for example, following organ transplant), those persons afflicted with human immunodeficiency syndrome (HIV) or acquired immune deficiency syndrome (AIDS), certain forms of anemia that deplete or destroy white blood cells, those persons receiving radiation or chemotherapy, or those persons afflicted with an inflammatory disorder. Additionally, subject of extreme young or old age are at increased risk. Any person who comes into physical contact or close physical proximity with an infected individual has an increased risk of developing an Influenza virus infection. Moreover, a subject is at risk of contracting an influenza infection due to proximity to an outbreak of the disease, e.g. subject resides in a densely-populated city or in close proximity to subjects having confirmed or suspected infections of Influenza virus, or choice of employment, e.g. hospital worker, pharmaceutical researcher, traveler to infected area, or frequent flier.

As used herein, the terms "treat", "treating", or "treatment" refer to the reduction or amelioration of the severity of at least one symptom or indication of influenza infection due to the administration of a therapeutic agent such as an antibody disclosed herein to a subject in need thereof. The terms include inhibition of progression of disease or of worsening of infection. The terms also include positive prognosis of disease, i.e., the subject may be free of infection or may have reduced or no viral titers upon administration of a therapeutic agent such as an antibody disclosed herein. The therapeutic agent may be administered at a therapeutic dose to the subject.

The terms "prevent", "preventing" or "prevention" refer to inhibition of manifestation of influenza infection or any symptoms or indications of influenza infection upon administration of an antibody disclosed herein. The term includes prevention of spread of infection in a subject exposed to the virus or at risk of having influenza infection.

As used herein a "protective effect" may be demonstrated by any standard procedure known in the art to determine whether an agent such as an anti-viral agent, or an antibody such as an anti-influenza-HA antibody disclosed herein can provide any one or more of, e.g., an increase in survival in a population of subjects after exposure to an infectious agent (relative to a comparable population of subjects that were untreated and also exposed to the infectious agent), a decrease in viral load (relative to the subject prior to treatment), or amelioration of at least one symptom associated with the infectious agent (relative to the subject prior to treatment).

As used herein, the term "anti-viral drug" refers to any anti-infective drug or therapy used to treat, prevent, or ameliorate a viral infection in a subject. The term "anti-viral drug" includes, but is not limited to TAMIFLU® (Oseltamivir), RELENZA® (Zanamivir), baloxavir, marboxil, ribavirin, or interferon-alpha2b. An "anti-viral drug" also includes anti-viral antibodies. For example, an anti-viral drug can be an antibody used to treat, prevent, or ameliorate an influenza infection (e.g., influenza A, influenza B, or both). Such an antibody can target hemagglutinin from influenza A, influenza B, or both. In the present disclosure, the infection to be treated is caused by an influenza virus.

General Description

Influenza is an infectious disease caused by RNA viruses of the family Orthomyxoviridae (the influenza viruses). Influenza viruses are classified based on core protein into four genera A, B, C, and D that are further divided into subtypes determined by the viral envelope glycoproteins hemagglutinin (HA) and neuraminidase (NA). Influenza B viruses formed a homogenous group that started to diverge into two antigenically distinguishable lineages in the 1970s, B/Victoria/2/87 and B/Yamagata/16/88, now known as the Victoria and Yamagata lineages. Influenza A viruses infect a range of mammalian and avian species, whereas type B and C infections are largely restricted to humans. Influenza D primarily infects cattle but not humans. Only types A and B cause human disease of any concern.

High mutation rates and frequent genetic reassortments of the influenza viruses contribute to great variability of the HA and NA antigens. Minor point mutations causing small changes ("antigenic drift") occur relatively often. Antigenic drift enables the virus to evade immune recognition, resulting in repeated influenza outbreaks during interpandemic years. Major changes in the HA antigen ("antigenic shift") are caused by reassortment of genetic material from different influenza subtypes. Antigenic shifts resulting in new pandemic strains are rare events, occurring through reassortment between animal and human subtypes, for example in co-infected pigs.

HA is synthesized as a homo-trimeric precursor polypeptide HA0. Each monomer can be independently cleaved post-translationally to form two polypeptides, HA1 and HA2, linked by a single disulphide bond. The larger N-terminal fragment (HAL 320-330 amino acids) forms a membrane-distal globular domain that contains the receptor-binding site and most determinants recognized by virus-neutralizing antibodies. The HA1 polypeptide of HA is responsible for the attachment of virus to the cell surface. The smaller C-terminal portion (HA2, approximately 180 amino acids) forms a stem-like structure that anchors the globular domain to the cellular or viral membrane. The HA2 polypeptide mediates the fusion of viral and cell membranes in endosomes, allowing the release of the ribonucleoprotein complex into the cytoplasm.

Despite decades of research, there are no marketed antibodies that broadly neutralize or inhibit influenza B virus infection or attenuate disease caused by influenza B virus. Therefore, there is a need to identify new antibodies that neutralize multiple subtypes of influenza B virus and can be used as medicaments for prevention or therapy of influenza B infection.

Passive immunotherapy for prophylaxis or treatment of infectious diseases has been used for more than a century, usually in the form of convalescent human sera that contains high titers of neutralizing antibodies (Good et al. 1991; Cancer 68: 1415-1421). Today, multiple purified monoclonal antibodies are currently in preclinical and clinical development for use as anti-microbials (Marasco et al. 2007; Nature Biotechnology 25: 1421-1434).

The inventors have described herein fully human antibodies and antigen-binding fragments thereof that specifically bind to influenza hemagglutinin and modulate the interaction of influenza virus with host cells. The anti-influenza B HA antibodies may bind to the influenza B virus HA with high affinity. In certain embodiments, the antibodies disclosed herein are blocking antibodies wherein the antibodies may bind to influenza HA and block the attachment to and/or entry of the virus into host cells. In some embodiments, the blocking antibodies may block the binding of influenza virus to cells and as such may inhibit or neutralize viral infectivity of host cells. In some embodiments, the blocking antibodies may be useful for treating a subject suffering from an influenza virus infection. The antibodies when administered to a subject in need thereof may reduce the infection by a virus such as influenza in the subject. They may be used to decrease viral loads in a subject relative to an untreated subject. They may be used alone or as adjunct therapy with other therapeutic moieties or modalities known in the art for treating a viral infection. In certain embodiments, these antibodies may bind to an epitope in the stem region of the viral HA. Furthermore, the identified antibodies can be used prophylactically (before infection) to protect an animal (e.g., a mammal) from infection, or can be used therapeutically (after infection is established) to ameliorate a previously established infection, or to ameliorate at least one symptom associated with the infection.

The full-length amino acid sequences of exemplary Influenza B HAs are shown in GenBank as accession number AAA43697.1, (from B/Victoria/2/87, see also SEQ ID NO: 21), accession number AAD02807.1 (partial sequence from B/Nanchang/3451/93, see also SEQ ID NO: 22), accession number ABN50712.1 (from B/Singapore/11/1994, see also SEQ ID NO: 23), and accession number ACA33493.1 (from B/Florida/4/2006, see also SEQ ID NO: 24).

In certain embodiments, the antibodies are obtained from mice immunized with a primary immunogen, such as a full-length influenza B HA or with a recombinant form of influenza B HA or fragments thereof followed by immunization with a secondary immunogen, or with an immunogenically active fragment of influenza B HA. In certain embodiments, the antibodies are obtained from mice immunized with an influenza vaccine composition followed by booster immunization with one or more recombinantly produced HA peptides. For example, an antibody can be obtained by immunizing mice with B/Victoria/2/87 followed by B/Yamagata/16/88 and then again with B/Victoria/2/87; or by immunizing mice with B/Yamagata/16/88 followed by B/Victoria/2/87 and then again with B/Yamagata/16/88. In some aspects, the B/Yamagata strain can be replaced with B/Maryland/03/2008 or B/Florida/4/2006 or B/Nanchang/3451/93 or B/Singapore/11/1994. Mice can be boosted with a mixture of DNAs encoding the HA from B/Victoria/2/87, B/Yamagata/16/88, B/Maryland/03/2008, B/Nanchang/3451/93, B/Singapore/11/1994, and/or B/Florida/4/2006, for example, with a 1:1 mixture of DNAs encoding the HA from B/Victoria/2/87 and B/Yamagata/16/88.

The immunogen may be a biologically active and/or immunogenic fragment of influenza B HA or DNA encoding the active fragment thereof. The fragment may be derived from the stem region of the HA protein.

The peptides may be modified to include addition or substitution of certain residues for tagging or for purposes of conjugation to carrier molecules, such as, KLH. For example, a cysteine may be added at either the N terminal or C terminal end of a peptide, or a linker sequence may be added to prepare the peptide for conjugation to, for example, KLH for immunization.

Certain anti-influenza B HA antibodies disclosed herein are able to bind to and neutralize the activity of influenza B HA, as determined by in vitro or in vivo assays. The ability of the antibodies to bind to and neutralize the activity of influenza B HA and thus the attachment and/or entry of the virus into a host cell followed by the ensuing viral infection, may be measured using any standard method known to those skilled in the art, including binding assays, or activity assays, as described herein.

Non-limiting, exemplary in vitro assays for measuring binding activity are known to one skilled in the art. For example, the binding affinity and dissociation constants of anti-influenza B HA antibodies for influenza B HA can be determined by surface plasmon resonance using a Biacore instrument. Neutralization assays can be used to determine infectivity of diverse strains of influenza B virus. Antibodies to influenza B HA can mediate complement dependent cytotoxicity (CDC) or can mediate antibody dependent cell-mediated cytotoxicity (ADCC) of virus-infected cells in vitro. Exemplary antibodies are capable of neutralizing an influenza B infection in vivo.

The antibodies specific for influenza B HA may contain no additional labels or moieties, or they may contain an N-terminal or C-terminal label or moiety. In some embodiments, the label or moiety is biotin. In a binding assay, the location of a label (if any) may determine the orientation of the peptide relative to the surface upon which the peptide is bound. For example, if a surface is coated with avidin, a peptide containing an N-terminal biotin will be oriented such that the C-terminal portion of the peptide will be distal to the surface. In some embodiments, the label may be a radionuclide, a fluorescent dye or a MRI-detectable label. In certain embodiments, such labeled antibodies may be used in diagnostic assays including imaging assays.

Antibodies and Antigen-Binding Fragments of Antibodies
Antibodies

The term "antibody", as used herein, is intended to refer to immunoglobulin molecules comprised of four polypeptide chains, two heavy (H) chains and two light (L) chains inter-connected by disulfide bonds (i.e., "full antibody molecules"), as well as multimers thereof (e.g. IgM) or antigen-binding fragments thereof. Each heavy chain is comprised of a heavy chain variable region ("HCVR" or "$V_H$") and a heavy chain constant region (comprised of domains $C_H1$, $C_H2$ and $C_H3$). Each light chain is comprised of a light chain variable region ("LCVR or "$V_L$") and a light chain constant region ($C_L$). The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. An amino acid consensus sequence may be defined based on a side-by-side analysis of two or more CDRs.

The term "human antibody", as used herein, is intended to include antibodies having variable and constant regions derived from human germline immunoglobulin sequences. The human monoclonal antibodies may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include monoclonal antibodies in which CDR sequences derived from the germline of another mammalian species (e.g., mouse), have been grafted onto human FR sequences. The term includes antibodies recombinantly produced in a non-human mammal, or in cells of a non-human mammal. The term is not intended to include antibodies isolated from or generated in a human subject.

The term "recombinant", as used herein, refers to antibodies or antigen-binding fragments thereof created, expressed, isolated or obtained by technologies or methods known in the art as recombinant DNA technology which include, e.g., DNA splicing and transgenic expression. The term refers to antibodies expressed in a non-human mammal (including transgenic non-human mammals, e.g., transgenic mice), or a cell (e.g., CHO cells) expression system or isolated from a recombinant combinatorial human antibody library.

The term "specifically binds," or "binds specifically to", or the like, means that an antibody or antigen-binding fragment thereof forms a complex with an antigen that is relatively stable under physiologic conditions. Specific binding can be characterized by an equilibrium dissociation constant of at least about $1\times10^{-8}$ M or less (e.g., a smaller $K_D$ denotes a tighter binding). Methods for determining whether two molecules specifically bind are well known in the art and include, for example, equilibrium dialysis, surface plasmon resonance, and the like. As described herein, antibodies have been identified by real-time, label free bio-layer interferometry assay on an Octet® HTX biosensor, which bind specifically to influenza-HA. Moreover, multi-specific antibodies that bind to one domain in influenza-HA and one or more additional antigens or a bispecific that binds to two different regions of influenza-HA are nonetheless considered antibodies that "specifically bind", as used herein.

The term "high affinity" antibody refers to those monoclonal antibodies having a binding affinity to influenza-HA, expressed as $K_D$, of at least $10^{-8}$ M; at least about $10^{-9}$ M; at least about $10^{-10}$M; or at least about $10^{-11}$ M, as measured by real-time, label free bio-layer interferometry assay, e.g., an Octet® HTX biosensor, or by surface plasmon resonance, e.g., BIACORE™, or by solution-affinity ELISA.

By the term "slow off rate", "Koff" or "kd" is meant an antibody that dissociates from influenza-HA, with a rate constant of $1\times10^{-3}$ $s^{-1}$ or less, or $1\times10^{-4}$ $s^{-1}$ or less, as determined by real-time, label free bio-layer interferometry assay, e.g., an Octet® HTX biosensor, or by surface plasmon resonance, e.g., BIACORE™.

The term "$K_D$", as used herein, is intended to refer to the equilibrium dissociation constant of a particular antibody-antigen interaction.

The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. The terms "antigen-binding fragment" of an antibody, or "antibody fragment", as used herein, refers to one or more fragments of an antibody that retain the ability to bind to Influenza HA.

In specific embodiments, antibody or antibody fragments provided herein may be conjugated to a moiety such a ligand or a therapeutic moiety ("immunoconjugate"), such as an anti-viral drug, a second anti-influenza antibody, or any other therapeutic moiety useful for treating an infection caused by influenza virus.

An "isolated antibody", as used herein, is intended to refer to an antibody that is substantially free of other antibodies (Abs) having different antigenic specificities (e.g., an isolated antibody that specifically binds influenza-HA, or a fragment thereof, is substantially free of Abs that specifically bind antigens other than influenza-HA).

A "blocking antibody" or a "neutralizing antibody", as used herein (or an "antibody that neutralizes influenza-HA activity" or "antagonist antibody"), is intended to refer to an antibody whose binding to influenza-HA results in inhibition of at least one biological activity of influenza-HA. For example, an antibody provided herein may prevent or block influenza attachment to, or entry into a host cell. In addition, a "neutralizing antibody" is one that can neutralize, i.e., prevent, inhibit, reduce, impede or interfere with, the ability of a pathogen to initiate and/or perpetuate an infection in a host. The terms "neutralizing antibody" and "an antibody that neutralizes" or "antibodies that neutralize" are used interchangeably herein. These antibodies can be used, alone or in combination, as prophylactic or therapeutic agents with other anti-viral agents upon appropriate formulation, or in association with active vaccination, or as a diagnostic tool.

Antigen-Binding Fragments

Unless specifically indicated otherwise, the term "antibody," as used herein, shall be understood to encompass antibody molecules comprising two immunoglobulin heavy chains and two immunoglobulin light chains (i.e., "full antibody molecules") as well as antigen-binding fragments thereof. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. The terms "antigen-binding fragment" of an antibody, or "antibody fragment", as used herein, refers to one or more fragments of an antibody that retain the ability to specifically bind to influenza B HA. An antibody fragment may include a Fab fragment, a F(ab')$_2$ fragment, a Fv fragment, a dAb fragment, a fragment containing a CDR, or an isolated CDR. In certain embodiments, the term "antigen-binding fragment" refers to a polypeptide fragment of a multi-specific antigen-binding molecule. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and (optionally) constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR, which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody disclosed herein include: (i) $V_H$-$C_H$1; (ii) $V_H$-$C_H$2; (iii) $V_H$-$C_H$3; (iv) $V_H$-$C_H$1-$C_H$2; (V) $V_H$-$C_H$1-$C_H$2-$C_H$3; (vi) $V_H$-$C_H$2-$C_H$3; (vii) $V_H$-$C_L$; (viii) $V_L$-$C_H$1; (ix) $V_L$-$C_H$2; (x) $V_L$-$C_H$3; (xi) $V_L$-$C_H$1-$C_H$2; (xii) $V_L$-$C_H$1-$C_H$2-$C_H$3; (xiii) $V_L$-$C_H$2-$C_H$3; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids, which result in a flexible or semi-flexible linkage between adjacent variable and/or constant domains in a single polypeptide molecule. Moreover, an antigen-binding fragment of an antibody disclosed herein may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen-binding fragments may be mono-specific or multi-specific (e.g., bi-specific). A multi-specific antigen-binding fragment of an antibody will typically comprise at least two different variable domains, wherein each variable domain is capable of specifically binding to a separate antigen or to a different epitope on the same antigen. Any multi-specific antibody format, including the exemplary bi-specific antibody formats disclosed herein, may be adapted for use in the context of an antigen-binding fragment of an antibody disclosed herein using routine techniques available in the art.

Modifications to Antibodies and Antigen-Binding Fragments Thereof

In certain embodiments, the framework regions of the antibody (or antigen binding fragment thereof) may be identical to the human germline sequences, for example, identical to the sequences of the antibodies provided herein, or may be naturally or artificially modified. One or more amino acids in a given framework region (or one or more framework regions) can be substituted, and the substitution(s) can be conservative or non-conservative substitutions. Substitution of one or more CDR residues or omission of one or more CDRs is also possible. Antibodies have been described in the scientific literature in which one or two CDRs can be dispensed with for binding. Padlan et al. (1995 FASEB J. 9:133-139) analyzed the contact regions between antibodies and their antigens, based on published crystal structures, and concluded that only about one fifth to one third of CDR residues actually contact the antigen. Padlan also found many antibodies in which one or two CDRs had no amino acids in contact with an antigen (see also, Vajdos et al. 2002 J Mol Biol 320:415-428). Thus, the antibodies provided herein can be effectively modified in the CDR regions and/or the framework regions, as long as the modified antibody maintains one or more desirable characteristics, e.g. the antibody or antigen-binding fragment thereof binds to influenza B HA with an $EC_{50}$ of less than about $10^{-10}$ M; and/or demonstrates an increase in survival in an influenza-infected animal after administration to said influenza-infected animal, as compared to a comparable influenza-infected animal without said administration.

Modifications to a given CDR can be made relative to a CDR sequence from an antibody provided herein, and the modifications can include conservative or non-conservative substitutions. Desirable substitutions can be determined by molecular modeling and/or empirically. For example, one or more CDR residues can be substituted with an amino acid occupying the corresponding position in another human antibody sequence or a consensus of such sequences.

Furthermore, an antigen-binding fragment thereof can be an antibody disclosed herein but modified to omit one or more CDRs and/or one or more framework regions, as long as the modified antibody (a.k.a., antigen-binding fragment) maintains binding to influenza B HA.

CDR residues not contacting antigen can be identified based on previous studies (for example, residues H60-H65 in HCDR2 are often not required), from regions of Kabat CDRs lying outside Chothia CDRs, by molecular modeling, and/or empirically. An antibody or antigen-binding fragment thereof provided herein can be modified to remove or replace a given CDR, particularly one that does not contact antigen. Light chain CDRs can be replaced with, for example, universal light chain CDRs.

The fully human anti-influenza-HA monoclonal antibodies provided herein may comprise one or more amino acid substitutions, insertions and/or deletions in the framework and/or CDR regions of the heavy and light chain variable domains as compared to the corresponding germline sequences, or as compared to the sequences provided herein. Such modifications or mutations can be readily ascertained by comparing the amino acid sequences disclosed herein to germline sequences available from, for example, public antibody sequence databases, or by comparing the amino acid sequences to those of the antibodies provided herein, for example, any one of the antibody sequences provided in Table 1.

The present disclosure includes antibodies, and antigen-binding fragments thereof, which are derived from any of the amino acid sequences disclosed herein, wherein one or more amino acids within one or more framework regions and/or CDRs are modified, as long as the modified antibody maintains one or more desirable characteristics, e.g. the antibody or antigen-binding fragment thereof binds to influenza B HA with an $EC_{50}$ of less than about $10^{-10}$ M; and/or demonstrates an increase in survival in an influenza-infected animal after administration to said influenza-infected animal, as compared to a comparable influenza-infected animal without said administration. Once obtained, antibodies and antigen-binding fragments that contain one or more modifications to a framework region and/or CDR can be easily tested for one or more desired properties such as, improved binding specificity, increased binding affinity, improved or enhanced antagonistic or agonistic biological properties (as the case may be), reduced immunogenicity, etc.

The present disclosure also includes antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual modifications or germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies disclosed herein may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired properties such as, improved binding specificity, increased binding affinity, improved or enhanced antagonistic or agonistic biological properties (as the case may be), reduced immunogenicity, etc. Antibodies and antigen-binding fragments obtained in this general manner are encompassed within the present disclosure.

The present disclosure provides antibodies with "substantial identity" or "substantial similarity" to the sequences provided herein in the CDR or framework regions. Differences in sequences, for example, the difference between a sequence provided in Table 1 or Table 2 and a modified sequence based thereon, are noted by "substantial identity" or "substantial similarity".

The term "substantial identity" or "substantially identical," when referring to a nucleic acid or fragment thereof, indicates that, when optimally aligned with another nucleic acid (or the complementary strand of the other nucleic acid), there is nucleotide sequence identity in %, for example, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% of the nucleotide bases, as measured by any well-known algorithm of sequence identity, such as FASTA, BLAST or GAP, as discussed below. A nucleic acid molecule having substantial identity to a reference nucleic acid molecule may, in certain instances, encode a polypeptide having the same or substantially similar amino acid sequence as the polypeptide encoded by the reference nucleic acid molecule.

As applied to polypeptides, the term "substantial similarity" or "substantially similar" means that two peptide sequences, when optimally aligned, such as by the programs GAP or BESTFIT using default gap weights, share at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% sequence identity. In some aspects, residue positions, which are not identical, differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent or degree of similarity may be adjusted upwards to correct for the conservative nature of the substitution. Means for making this adjustment are well known to those of skill in the art. See, e.g., Pearson (1994) Methods Mol. Biol. 24: 307-331, which is herein incorporated by reference. Examples of groups of amino acids that have side chains with similar chemical properties include 1) aliphatic side chains: glycine, alanine, valine, leucine and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartate and glutamate, and 7) sulfur-containing side chains: cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443 45, herein incorporated by reference. A "moderately conservative" replacement is any change having a nonnegative value in the PAM250 log-likelihood matrix.

Sequence identity and/or similarity for polypeptides is typically measured using sequence analysis software. Protein analysis software matches similar sequences using measures of similarity assigned to various substitutions, deletions and other modifications, including conservative amino acid substitutions. For instance, GCG software contains programs such as GAP and BESTFIT which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA with default or recommended parameters; a program in GCG Version 6.1. FASTA (e.g., FASTA2 and FASTA3) provides alignments and percent sequence identity of the regions of the best overlap between the query and search sequences (Pearson (2000) supra). Sequences also can be compared using the Smith-Waterman homology search algorithm using an affine gap search with a gap open penalty of 12 and a gap extension penalty of 2, BLOSUM matrix of 62. Another preferred algorithm when comparing a sequence disclosed herein to a database containing a large number of sequences from different organisms is the computer program BLAST, especially BLASTP or TBLASTN, using default parameters. See, e.g., Altschul et al. (1990) J. Mol. Biol. 215: 403-410 and (1997) Nucleic Acids Res. 25:3389-3402, each of which is herein incorporated by reference.

Provided herein are fully human anti-influenza-HA monoclonal antibodies comprising variants of any of the HCVR, LCVR, and/or CDR amino acid sequences disclosed herein having one or more substitutions (e.g., conservative substitutions). For example, the present disclosure includes anti-influenza B-HA antibodies having HCVR, LCVR, and/or CDR amino acid sequences with, e.g., 20 or fewer, 19 or fewer, 18 or fewer, 17 or fewer, 16 or fewer, 15 or fewer, 14 or fewer, 13 or fewer, 12 or fewer, 11 or fewer, 10 or fewer, 9 or fewer, 8 or fewer, 7 or fewer, 6 or fewer, 5 or fewer, 4 or fewer, 3 or fewer, 2 or fewer, or 1 amino acid substitutions relative to any of the HCVR, LCVR, and/or CDR (e.g., HCDR1, HCDR2, HCDR3, LCDR1, LCDR2, or LCDR3) amino acid sequences disclosed herein. For example, an anti-influenza B-HA antibody can comprise 20, 19, 18, 17, 16, 15, 14 13, 12, 11, 10, 9, 8, 7, 6, 5, 4, 3, 2, or 1 amino acid substitutions (e.g., conservative amino acid substitutions) relative to any of the HCVR, LCVR, and/or CDR (e.g., HCDR1, HCDR2, HCDR3, LCDR1, LCDR2, or LCDR3) amino acid sequences disclosed herein.

Illustratively, provided herein are antibodies, or antigen-binding fragments thereof, which specifically bind influenza B HA, comprising an HCVR amino acid sequence differing from SEQ ID NO: 2 by at least 1 to at most 50 conservative amino acid substitutions, for example by at least 10 to at most 40 conservative amino acid substitutions, or by at least 20 to at most 50 conservative amino acid substitutions, or by at least 20 to at most 40 conservative amino acid substitutions. Also provided herein are antibodies, or antigen-binding fragments thereof, which specifically bind influenza B HA, comprising an LCVR amino acid sequence differing from SEQ ID NO: 10 by at least 1 to at most 50 conservative amino acid substitutions, for example by at least 10 to at most 40 conservative amino acid substitutions, or by at least 20 to at most 50 conservative amino acid substitutions, or by at least 20 to at most 40 conservative amino acid substitutions. Such substitutions can be in the framework regions or in the CDRs and maintain specificity of the antibody, or antigen-binding fragment thereof, for binding to influenza B HA.

Also provided herein are antibodies, or antigen-binding fragments thereof, comprising an HCDR1 having an amino acid sequence differing from SEQ ID NO: 4 by 1, or 2, or 3 amino acid substitutions (e.g., conservative amino acid substitutions). Provided herein are antibodies, or antigen-binding fragments thereof, comprising an HCDR2 having an amino acid sequence differing from SEQ ID NO: 6 by 1, or 2, or 3 amino acid substitutions (e.g., conservative amino acid substitutions). Provided herein are antibodies, or antigen-binding fragments thereof, comprising an HCDR3 having an amino acid sequence differing from SEQ ID NO: 8 by 1, or 2, or 3 amino acid substitutions (e.g., conservative amino acid substitutions). Provided herein are antibodies, or antigen-binding fragments thereof, comprising an LCDR1 having an amino acid sequence differing from SEQ ID NO: 12 by 1, or 2, or 3 amino acid substitutions (e.g., conservative amino acid substitutions). Provided herein are antibodies, or antigen-binding fragments thereof, comprising an LCDR2 having an amino acid sequence differing from SEQ ID NO: 14 by 1, or 2, or 3 amino acid substitutions (e.g., conservative amino acid substitutions). Provided herein are antibodies, or antigen-binding fragments thereof, comprising an LCDR3 having an amino acid sequence differing from SEQ ID NO: 16 by 1, or 2, or 3 amino acid substitutions (e.g., conservative amino acid substitutions).

The present disclosure also provides antibodies, or antigen-binding fragments thereof, comprising an HCDR3 and an LCDR3 amino acid sequence pair (HCDR3/LCDR3) differing from SEQ ID NOs: 8/16 by at least 1, or at least 2, or at least 3, or at least 4, or at least 5, or at least 6 amino acid substitutions (e.g., conservative amino acid substitutions).

The present disclosure also provides antibodies, or antigen-binding fragments thereof, comprising a set of six CDRs (i.e., HCDR1-HCDR2-HCDR3-LCDR1-LCDR2-LCDR3) contained within HCVR/LCVR amino acid sequence of the exemplary anti-influenza B HA antibody shown in Table 1. In certain embodiments, the HCDR1-HCDR2-HCDR3-LCDR1-LCDR2-LCDR3 amino acid sequence set differs from SEQ ID NOs: 4-6-8-12-14-16 by at most 20 conservative amino acid substitutions, for example, by at most 1, or by at most 2, or by at most 3, or by at most 3, or by at most 4, or by at most 5, or by at most 6, or by at most 7, or by at most 8, or by at most 9, or by at most 10, or by at most 11, or by at most 12, or by at most 13, or by at most 14, or by at most 15, or by at most 16, or by at most 17, or by at most 18, or by at most 19 amino acid conservative amino acid substitutions.

Provided herein are antibodies, or antigen-binding fragments thereof, comprising an HCVR comprising an amino acid sequence according to Table 1, or a substantially similar sequence thereof having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% sequence identity thereto.

Provided herein are antibodies, or antigen-binding fragments thereof, comprising an LCVR comprising an amino acid sequence according to Table 1, or a substantially similar sequence thereof having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% sequence identity thereto.

Provided herein are antibodies, or antigen-binding fragments thereof, comprising an HCVR/LCVR amino acid sequence pair of SEQ ID NOs: 2/10, or a substantially similar sequence thereof having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% sequence identity thereto.

The present disclosure also provides antibodies, or antigen-binding fragments thereof, comprising a heavy chain CDR1 (HCDR1) comprising an amino acid sequence of SEQ ID NO: 4, or a substantially similar sequence thereof having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% sequence identity thereto.

The present disclosure also provides antibodies, or antigen-binding fragments thereof, comprising a heavy chain CDR2 (HCDR2) comprising an amino acid sequence of SEQ ID NO: 6, or a substantially similar sequence thereof having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% sequence identity thereto.

The present disclosure also provides antibodies, or antigen-binding fragments thereof, comprising a heavy chain CDR3 (HCDR3) comprising an amino acid sequence of SEQ ID NO: 8, or a substantially similar sequence thereof having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% sequence identity thereto.

The present disclosure also provides antibodies, or antigen-binding fragments thereof, comprising a light chain CDR1 (LCDR1) comprising an amino acid sequence of SEQ ID NO: 12, or a substantially similar sequence thereof having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% sequence identity thereto.

The present disclosure also provides antibodies, or antigen-binding fragments thereof, comprising a light chain CDR2 (LCDR2) comprising an amino acid sequence of SEQ ID NO: 14, or a substantially similar sequence thereof having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% sequence identity thereto.

The present disclosure also provides antibodies, or antigen-binding fragments thereof, comprising a light chain CDR3 (LCDR3) comprising an amino acid sequence of SEQ ID NO: 16, or a substantially similar sequence thereof having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% sequence identity thereto.

The present disclosure also provides antibodies, or antigen-binding fragments thereof, comprising an HCDR3 and an LCDR3 amino acid sequence pair (HCDR3/LCDR3) comprising SEQ ID NOs: 8/16, or a substantially similar sequence thereof having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% sequence identity thereto.

Preparation of Human Antibodies

Methods for generating human antibodies in transgenic mice are known in the art. Any such known methods can be used in the context disclosed herein to make human antibodies that specifically bind to Influenza B HA. An immunogen comprising any one of the following can be used to generate antibodies to influenza B HA. In certain embodiments, the antibodies are obtained from mice immunized with a full length, native influenza B HA (See, for example, Gen Bank accession numbers AAA43697.1. or ACA33493.1, or with a live attenuated or inactivated virus, or with DNA encoding the protein or fragment thereof. Alternatively, the influenza B HA protein or a fragment thereof may be produced using standard biochemical techniques and modified and used as an immunogen. In some embodiments, the immunogen may be a recombinantly produced influenza B HA protein or fragment thereof. In certain embodiments, the immunogen may be an influenza virus vaccine. In certain embodiments, one or more booster injections may be administered. In certain embodiments, the booster injections may comprise one or more influenza virus strains, or hemagglutinins derived from these strains, e.g., B/Victoria/2/87 followed by B/Yamagata/16/88 and then again with B/Victoria/2/87; or B/Yamagata/16/88 followed by B/Victoria/2/87 and then again with B/Yamagata/16/88. In some aspects, the B/Yamagata strain is replaced with B/Maryland/03/2008 or B/Nanchang/3451/93 or B/Florida/4/2006. All mice can be boosted with a mixture of DNAs encoding the HA from B/Victoria/2/87, B/Yamagata/16/88, B/Maryland/03/2008, and/or B/Florida/4/2006. In certain embodiments, the booster injections may contain a mixture of the influenza strains, or a mixture of the hemagglutinins derived from the strains, or the DNA encoding the HAs. In certain embodiments, the immunogen may be a recombinant influenza HA peptide expressed in *E. coli* or in any other eukaryotic or mammalian cells such as Chinese hamster ovary (CHO) cells or influenza virus itself.

Using VELOCIMMUNE® technology (see, for example, U.S. Pat. No. 6,596,541, Regeneron Pharmaceuticals, VELOCIMMUNE®) or any other known method for generating monoclonal antibodies, high affinity chimeric antibodies to influenza B HA are initially isolated having a human variable region and a mouse constant region. The VELOCIMMUNE® technology involves generation of a transgenic mouse having a genome comprising human heavy and light chain variable regions operably linked to endogenous mouse constant region loci such that the mouse produces an antibody comprising a human variable region and a mouse constant region in response to antigenic stimulation. The DNA encoding the variable regions of the heavy and light chains of the antibody are isolated and operably linked to DNA encoding the human heavy and light chain constant regions. The DNA is then expressed in a cell capable of expressing the fully human antibody.

Generally, a VELOCIMMUNE® mouse is challenged with the antigen of interest, and lymphatic cells (such as B-cells) are recovered from the mice that express antibodies. The lymphatic cells may be fused with a myeloma cell line to prepare immortal hybridoma cell lines, and such hybridoma cell lines are screened and selected to identify hybridoma cell lines that produce antibodies specific to the antigen of interest. DNA encoding the variable regions of the heavy chain and light chain may be isolated and linked to desirable isotypic constant regions of the heavy chain and light chain. Such an antibody protein may be produced in a cell, such as a CHO cell. Alternatively, DNA encoding the antigen-specific chimeric antibodies or the variable domains of the light and heavy chains may be isolated directly from antigen-specific lymphocytes.

Initially, high affinity chimeric antibodies are isolated having a human variable region and a mouse constant region. As in the experimental section below, the antibodies are characterized and selected for desirable characteristics, including affinity, selectivity, epitope, etc. The mouse constant regions are replaced with a desired human constant region to generate the fully human antibody, for example wild-type or modified IgG1 or IgG4. While the constant region selected may vary according to specific use, high affinity antigen-binding and target specificity characteristics reside in the variable region.

Bioequivalents

The anti-influenza B HA antibodies and antibody fragments disclosed herein encompass proteins having amino acid sequences that vary from those of the described antibodies, but that retain the ability to bind Influenza HA. Such variant antibodies and antibody fragments comprise one or more additions, deletions, or substitutions of amino acids when compared to parent sequence, but exhibit biological activity that is essentially equivalent to that of the described antibodies. Likewise, the antibody-encoding DNA sequences disclosed herein encompass sequences that comprise one or more additions, deletions, or substitutions of nucleotides when compared to the disclosed sequence, but that encode an antibody or antibody fragment that is essentially bioequivalent to an antibody or antibody fragment disclosed herein.

Two antigen-binding proteins, or antibodies, are considered bioequivalent if, for example, they are pharmaceutical equivalents or pharmaceutical alternatives whose rate and extent of absorption do not show a significant difference when administered at the same molar dose under similar experimental conditions, either single dose or multiple doses. Some antibodies will be considered equivalents or pharmaceutical alternatives if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied.

In some embodiments, two antigen-binding proteins are bioequivalent if there are no clinically meaningful differences in their safety, purity, or potency.

In some embodiments, two antigen-binding proteins are bioequivalent if a patient can be switched one or more times between the reference product and the biological product without an expected increase in the risk of adverse effects, including a clinically significant change in immunogenicity, or diminished effectiveness, as compared to continued therapy without such switching.

In some embodiments, two antigen-binding proteins are bioequivalent if they both act by a common mechanism or mechanisms of action for the condition or conditions of use, to the extent that such mechanisms are known.

Bioequivalence may be demonstrated by in vivo and/or in vitro methods. Bioequivalence measures include, e.g., (a) an in vivo test in humans or other mammals, in which the concentration of the antibody or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the antibody (or its target) is measured as a function of time; and (d) in a well-controlled clinical trial that establishes safety, efficacy, or bioavailability or bioequivalence of an antibody.

Bioequivalent variants of the antibodies may be constructed by, for example, making various substitutions of residues or sequences or deleting terminal or internal residues or sequences not needed for biological activity. For example, cysteine residues not essential for biological activity can be deleted or replaced with other amino acids to prevent formation of unnecessary or incorrect intramolecular disulfide bridges upon renaturation. In other contexts, bioequivalent antibodies may include antibody variants comprising amino acid changes, which modify the glycosylation characteristics of the antibodies, e.g., mutations that eliminate or remove glycosylation.

Anti-Influenza-HA Antibodies Comprising Fc Variants

According to certain embodiments disclosed herein, anti-influenza B HA antibodies are provided comprising an Fc domain comprising one or more mutations, which enhance or diminish antibody binding to the FcRn receptor, e.g., at acidic pH as compared to neutral pH. For example, the present disclosure includes anti-influenza-HA antibodies comprising a mutation in the $C_H2$ or a $C_H3$ region of the Fc domain, wherein the mutation(s) increases the affinity of the Fc domain to FcRn in an acidic environment (e.g., in an endosome where pH ranges from about 5.5 to about 6.0), relative to the same but unmodified antibody. Such mutations may result in an increase in serum half-life of the antibody, relative to the same but unmodified antibody, when administered to an animal. Non-limiting examples of such Fc modifications include, e.g., a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at position 428 and/or 433 (e.g., H/L/R/S/P/Q or K) and/or 434 (e.g., A, W, H, F or Y [N434A, N434W, N434H, N434F or N434Y]); or a modification at position 250 and/or 428; or a modification at position 307 or 308 (e.g., 308F, V308F), and 434. In some embodiments, the modification comprises a 428L (e.g., M428L) and 434S (e.g., N434S) modification; a 428L, 259I (e.g., V259I), and 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); and a 307 and/or 308 modification (e.g., 308F or 308P). In yet another embodiment, the modification comprises a 265A (e.g., D265A) and/or a 297A (e.g., N297A) modification.

For example, the present disclosure includes anti-influenza B HA antibodies comprising an Fc domain comprising one or more pairs or groups of mutations selected from the group consisting of: 250Q and 248L (e.g., T250Q and M248L); 252Y, 254T and 256E (e.g., M252Y, S254T and T256E); 428L and 434S (e.g., M428L and N434S); 257I and 311I (e.g., P257I and Q311I); 257I and 434H (e.g., P257I and N434H); 376V and 434H (e.g., D376V and N434H); 307A, 380A and 434A (e.g., T307A, E380A and N434A); and 433K and 434F (e.g., H433K and N434F). All possible combinations of the foregoing Fc domain mutations and other mutations within the antibody variable domains disclosed herein, are contemplated within the scope disclosed herein.

Provided herein are anti-influenza B HA antibodies comprising a chimeric heavy chain constant ($C_H$) region, wherein the chimeric $C_H$ region comprises segments derived from the $C_H$ regions of more than one immunoglobulin isotype. For example, the antibodies may comprise a chimeric $C_H$ region comprising part or all of a $C_H2$ domain derived from a human IgG1, human IgG2 or human IgG4 molecule, combined with part or all of a $C_H3$ domain derived from a human IgG1, human IgG2 or human IgG4 molecule. According to certain embodiments, the antibodies comprise a chimeric $C_H$ region having a chimeric hinge region. For example, a chimeric hinge may comprise an "upper hinge" amino acid sequence (amino acid residues from positions 216 to 227 according to EU numbering) derived from a human IgG1, a human IgG2 or a human IgG4 hinge region, combined with a "lower hinge" sequence (amino acid residues from positions 228 to 236 according to EU numbering) derived from a human IgG1, a human IgG2 or a human IgG4 hinge region. According to certain embodiments, the chimeric hinge region comprises amino acid residues derived from a human IgG1 or a human IgG4 upper hinge and amino acid residues derived from a human IgG2 lower hinge. An antibody comprising a chimeric $C_H$ region as described herein may, in certain embodiments, exhibit modified Fc effector functions without adversely affecting the therapeutic or pharmacokinetic properties of the antibody. (See, e.g., U.S. Provisional Appl. No. 61/759,578, filed Feb. 1, 2013, the disclosure of which is hereby incorporated by reference in its entirety).

Biological Characteristics of the Antibodies

In general, the antibodies disclosed herein function by binding to Influenza B HA. For example, the present disclosure includes antibodies and antigen-binding fragments of antibodies that bind Influenza B HA (e.g., at 25° C. or at 37° C.) with a $K_D$ of less than 10 nM, as measured by surface plasmon resonance in a Biacore instrument, or by real-time bio-layer interferometer based biosensor (Octet HTX assay). In certain embodiments, the antibodies or antigen-binding fragments thereof bind influenza B HA with a $K_D$ of less than about 5 nM, less than about 2 nM, less than about 1 nM, less than about 500 pM, less than 250 pM, or less than 100 pM, as measured by surface plasmon resonance, e.g., using the assay format as described herein, or a substantially similar assay.

The present disclosure also includes antibodies and antigen-binding fragments thereof that bind Influenza B HA with a dissociative half-life (t½) of greater than about 75 minutes as measured by surface plasmon resonance at 37° C., e.g., using an assay format as defined herein, or a substantially similar assay. In certain embodiments, the antibodies or antigen-binding fragments disclosed herein bind Influenza HA with a t½ of greater than about 200 minutes, greater than about 300 minutes, greater than about 400 minutes, greater than about 500 minutes, greater than about 600 minutes, greater than about 700 minutes, greater than about 800 minutes, greater than about 900 minutes, or greater than about 1000 minutes as measured by surface plasmon resonance at 25° C., e.g., using an assay format as defined herein (e.g., mAb-capture or antigen-capture format), or a substantially similar assay.

The present disclosure also includes antibodies or antigen-binding fragments thereof that neutralize the infectivity of influenza virus for its host cells. In some embodiments, the antibodies exhibit a neutralization potency against various representative influenza viruses, for example, B/Victoria/2/87, B/Yamagata/16/88, B/Maryland/03/2008, B/Nanchang/3451/93, and/or B/Florida/4/2006, with an $IC_{50}$ ranging from about 1 pM to about 800 nM, for example, an $IC_{50}$ ranging from about 1 pM to about 800 pM, an $IC_{50}$ ranging from about 1 pM to about 10 pM, an $IC_{50}$ ranging from about 10 pM to about 50 pM, an $IC_{50}$ ranging from about 1 pM to about 100 pM, an $IC_{50}$ ranging from about 10 pM to about 100 pM, an $IC_{50}$ ranging from about 100 pM to about 800 pM, or an $IC_{50}$ ranging from about 500 pM to about 800 pM, an $IC_{50}$ ranging from about 1 nM to about 10 nM, an $IC_{50}$ ranging from about 10 nM to about 50 nM, an $IC_{50}$ ranging from about 1 nM to about 100 nM, an $IC_{50}$ ranging from about 10 nM to about 100 nM, an $IC_{50}$ ranging from about 100 nM to about 800 nM, or an $IC_{50}$ ranging from about 500 nM to about 800 nM, in a microneutralization assay, or a substantially similar assay.

The present disclosure also includes antibodies or antigen-binding fragments thereof that bind to Influenza B infected cells at a sub-nM concentration, and demonstrate specific binding to HA (see Example 3).

The present disclosure also includes anti-influenza B HA antibodies that demonstrate an increase in protection (relative to an untreated subject), or potent neutralization of influenza B infection in vivo. Certain antibodies show protection when administered prophylactically (before infection; see Example 4). In some embodiments, one dose of anti-HA antibody at 5 mg/kg or 0.5 mg/kg administered at 5 days prior to infection resulted in 100% survival of mice when administered prophylactically, relative to mice treated with human IgG1 isotype control antibody.

Prophylactic treatment with anti-influenza B HA antibodies, or antigen-binding fragments thereof, can protect the mammal from infection by subsequent exposure to influenza virus, for example, or decrease the probability or risk of infection by subsequent exposure to influenza virus. Said protection is selected from the group consisting of amelioration, alleviation, or reduction in the severity, duration, or frequency of occurrence, of at least one symptom of influenza infection. In some aspects, the isolated antibody, when prophylactically administered to an animal (e.g., a mammal) prior to exposure to influenza virus (e.g., at least 2 days, at least 3 days, at least 4 days, at least 5 days, or 2 to 5 days prior to exposure to influenza virus), decreases the risk of influenza infection. The at least one symptom can be selected from the group consisting of headache, fever, aches, rhinorrhea (nasal congestion), chills, fatigue, weakness, sore throat, cough, shortness of breath, vomiting, diarrhea, pneumonia, bronchitis, and death.

In one embodiment, an isolated recombinant antibody or antigen-binding fragment thereof that specifically binds to influenza B HA has one or more of the following characteristics: (a) is a fully human monoclonal antibody; (b) binds to influenza B HA with an $EC_{50}$ of less than about $10^{-9}$, less than about $10^{-10}$M, less than about $10^{-11}$ M, less than about $10^{-12}$ M, or less than about $10^{-13}$ M; (c) demonstrates an increase in survival in an influenza-infected animal, as compared to a comparable influenza-infected animal without treatment with the isolated recombinant antibody or antigen-binding fragment thereof that specifically binds to influenza B HA; and/or (d) comprises (i) three heavy chain complementarity determining regions (CDRs) (HCDR1, HCDR2 and HCDR3) contained within a heavy chain variable region (HCVR) comprising the amino acid sequence set forth in SEQ ID NO: 2; and (ii) three light chain CDRs (LCDR1, LCDR2 and LCDR3) contained within a light chain variable region (LCVR) comprising the amino acid sequence set forth in SEQ ID NO: 10.

The antibodies disclosed herein may possess one or more of the aforementioned biological characteristics, or any combinations thereof. Other biological characteristics of the antibodies disclosed herein will be evident to a person of ordinary skill in the art from a review of the present disclosure including the working Examples herein.

Epitope Mapping and Related Technologies

The present disclosure includes anti-influenza B HA antibodies, which interact with one or more amino acids found within one or more domains of an influenza B HA molecule. The epitope to which the antibodies bind may consist of a single contiguous sequence of 3 or more (e.g., 3, 4, 5, 6, 7, 8, 9, 10, 11, 12, 13, 14, 15, 16, 17, 18, 19, 20, or more) amino acids located within an influenza HA molecule (e.g. a linear epitope in a domain). Alternatively, the epitope may consist of a plurality of non-contiguous amino acids (or amino acid sequences) located within an influenza B HA molecule (e.g. a conformational epitope).

Various techniques known to persons of ordinary skill in the art can be used to determine whether an antibody "interacts with one or more amino acids" within a polypeptide or protein. Exemplary techniques include, for example, routine cross-blocking assays, such as that described in Antibodies, Harlow and Lane (Cold Spring Harbor Press, Cold Spring Harbor, N.Y.). Other methods include alanine scanning mutational analysis, peptide blot analysis (Reineke (2004) Methods Mol. Biol. 248: 443-63), peptide cleavage analysis crystallographic studies and NMR analysis. In addition, methods such as epitope excision, epitope extraction and chemical modification of antigens can be employed (Tomer (2000) Prot. Sci. 9: 487-496). Another method that can be used to identify the amino acids within a polypeptide with which an antibody interacts is hydrogen/deuterium exchange detected by mass spectrometry. In general terms, the hydrogen/deuterium exchange method involves deuterium-labeling the protein of interest, followed by binding the antibody to the deuterium-labeled protein. Next, the protein/antibody complex is transferred to water and exchangeable protons within amino acids that are protected by the antibody complex undergo deuterium-to-hydrogen back-exchange at a slower rate than exchangeable protons within amino acids that are not part of the interface. As a result, amino acids that form part of the protein/antibody interface may retain deuterium and therefore exhibit relatively higher mass compared to amino acids not included in the interface. After dissociation of the antibody, the target protein is subjected to protease cleavage and mass spectrometry analysis, thereby revealing the deuterium-labeled residues which correspond to the specific amino acids with which the antibody interacts. See, e.g., Ehring (1999) Analytical Biochemistry 267: 252-259; Engen and Smith (2001) Anal. Chem. 73: 256A-265A.

The term "epitope" refers to a site on an antigen to which B and/or T cells respond. B-cell epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3 amino acids, or at least 4 amino acids, for example, at least 5, at least 6, at least 7, at least 8, at least 9, or at least 10 amino acids in a unique spatial conformation.

Modification-Assisted Profiling (MAP), also known as Antigen Structure-based Antibody Profiling (ASAP) is a method that categorizes large numbers of monoclonal antibodies (mAbs) directed against the same antigen according to the similarities of the binding profile of each antibody to chemically or enzymatically modified antigen surfaces (see US 2004/0101920, herein specifically incorporated by reference in its entirety). Each category may reflect a unique epitope either distinctly different from or partially overlapping with epitope represented by another category. This technology allows rapid filtering of genetically identical antibodies, such that characterization can be focused on genetically distinct antibodies. When applied to hybridoma screening, MAP may facilitate identification of rare hybridoma clones that produce monoclonal antibodies having the desired characteristics. MAP may be used to sort the antibodies provided herein into groups of antibodies binding different epitopes.

In certain embodiments, the influenza virus A HA antibodies or antigen-binding fragments thereof bind an epitope within any one or more of the regions exemplified in influenza HA, either in natural form, or recombinantly produced, or to a fragment thereof.

The present disclosure includes anti-influenza B HA antibodies that bind to the same epitope, or a portion of the epitope. Likewise, the present disclosure also includes anti-influenza B HA antibodies that compete for binding to influenza B HA or a fragment thereof with any of the specific exemplary antibodies described herein. For example, the present disclosure includes anti-influenza B HA antibodies that cross-compete for binding to influenza B HA with one or more antibodies obtained from those antibodies described in Table 1.

One can determine whether an antibody binds to the same epitope as, or competes for binding with, a reference anti-influenza B HA antibody by using known methods. For example, to determine if a test antibody binds to the same epitope as a reference anti-influenza B HA antibody, the reference antibody is allowed to bind to an influenza B HA or peptide under saturating conditions. Next, the ability of a test antibody to bind to the influenza B HA molecule is assessed. If the test antibody is able to bind to influenza B HA following saturation binding with the reference anti-influenza B HA antibody, it can be concluded that the test antibody binds to a different epitope than the reference anti-influenza B HA antibody. On the other hand, if the test antibody is not able to bind to the influenza B HA following saturation binding with the reference anti-influenza B HA antibody, then the test antibody may bind to the same epitope as the epitope bound by the reference anti-influenza B HA antibody.

To determine if an antibody competes for binding with a reference anti-influenza B HA antibody, the above-described binding methodology is performed in two orientations: In a first orientation, the reference antibody is allowed to bind to an influenza B HA under saturating conditions followed by assessment of binding of the test antibody to the influenza B HA molecule. In a second orientation, the test antibody is allowed to bind to an influenza B HA molecule under saturating conditions followed by assessment of binding of the reference antibody to the influenza B HA molecule. If, in both orientations, only the first (saturating) antibody is capable of binding to the influenza B HA molecule, then it is concluded that the test antibody and the reference antibody compete for binding to influenza B HA. As will be appreciated by a person of ordinary skill in the art, an antibody that competes for binding with a reference antibody may not necessarily bind to the identical epitope as the reference antibody, but may sterically block binding of the reference antibody by binding an overlapping or adjacent epitope.

Two antibodies bind to the same or overlapping epitope if each competitively inhibits (blocks) binding of the other to the antigen. That is, a 1-, 5-, 10-, 20- or 100-fold excess of one antibody inhibits binding of the other by at least 50%, for example, 75%, 90% or even 99% as measured in a competitive binding assay (see, e.g., Junghans et al., Cancer Res. 1990 50:1495-1502). Alternatively, two antibodies have the same epitope if essentially all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

Additional routine experimentation (e.g., peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using ELISA, RIA, surface plasmon resonance, flow cytometry or any other quantitative or qualitative antibody-binding assay available in the art.

Immunoconjugates

Contemplated herein is a human anti-influenza B HA monoclonal antibody conjugated to a therapeutic moiety ("immunoconjugate"), such as a toxoid or an anti-viral drug to treat influenza virus infection. As used herein, the term "immunoconjugate" refers to an antibody, which is chemically or biologically linked to a radioactive agent, a cytokine, an interferon, a target or reporter moiety, an enzyme, a peptide or protein or a therapeutic agent. The antibody may be linked to the radioactive agent, cytokine, interferon, target or reporter moiety, enzyme, peptide or therapeutic agent at any location along the molecule so long as it is able to bind its target. Examples of immunoconjugates include antibody drug conjugates and antibody-toxin fusion proteins. In one embodiment, the agent may be a second different antibody to Influenza-HA. In certain embodiments, the antibody may be conjugated to an agent specific for a virally infected cell. The type of therapeutic moiety that may be conjugated to the anti-influenza-HA antibody and will take into account the condition to be treated and the desired therapeutic effect to be achieved. Examples of suitable agents for forming immunoconjugates are known in the art; see for example, WO 05/103081.

Multi-Specific Antibodies

The antibodies disclosed herein may be mono-specific, bi-specific, or multi-specific. Multi-specific antibodies may be specific for different epitopes of one target polypeptide or may contain antigen-binding domains specific for more than one target polypeptide. See, e.g., Tutt et al., 1991, J. Immunol. 147:60-69; Kufer et al., 2004, Trends Biotechnol. 22:238-244.

Any of the multi-specific antigen-binding molecules provided herein, or variants thereof, may be constructed using standard molecular biological techniques (e.g., recombinant DNA and protein expression technology), as will be known to a person of ordinary skill in the art.

In some embodiments, influenza B HA-specific antibodies are generated in a bi-specific format (a "bi-specific" or "bispecific") in which variable regions binding to distinct domains of influenza B HA are linked together to confer dual-domain specificity within a single binding molecule. Appropriately designed bispecifics may enhance overall influenza B HA-protein inhibitory efficacy through increasing both specificity and binding avidity. Variable regions with specificity for individual domains, (e.g., segments of the N-terminal domain), or that can bind to different regions within one domain, are paired on a structural scaffold that allows each region to bind simultaneously to the separate epitopes, or to different regions within one domain. In one example for a bispecific, heavy chain variable regions ($V_H$) from a binder with specificity for one domain are recombined with light chain variable regions ($V_L$) from a series of binders with specificity for a second domain to identify non-cognate $V_L$ partners that can be paired with an original $V_H$ without disrupting the original specificity for that $V_H$. In this way, a single $V_L$ segment (e.g., $V_L1$) can be combined with two different $V_H$ domains (e.g., $V_H1$ and $V_H2$) to generate a bispecific comprised of two binding "arms" ($V_H1$-$V_L1$ and $V_H2$-$V_L1$). Use of a single $V_L$ segment reduces the complexity of the system and thereby simplifies and increases efficiency in cloning, expression, and purification processes used to generate the bispecific (See, for example, U.S. Ser. No. 13/022,759 and US2010/0331527).

Alternatively, antibodies that bind more than one domain and a second target, such as, but not limited to, for example, a second different anti-influenza B HA antibody, may be prepared in a bispecific format using techniques described herein, or other techniques known to those skilled in the art. Antibody variable regions binding to distinct regions may be linked together with variable regions that bind to relevant sites on, for example, the influenza virus, to confer dual-antigen specificity within a single binding molecule. Appropriately designed bispecifics of this nature serve a dual function. Variable regions with specificity for the extracellular domain are combined with a variable region with specificity for outside the extracellular domain and are paired on a structural scaffold that allows each variable region to bind to the separate antigens.

An exemplary bispecific antibody format that can be used in the context disclosed herein involves the use of a first immunoglobulin (Ig) $C_H3$ domain and a second Ig $C_H3$ domain, wherein the first and second Ig $C_H3$ domains differ from one another by at least one amino acid, and wherein at least one amino acid difference reduces binding of the bispecific antibody to Protein A as compared to a bispecific antibody lacking the amino acid difference. In one embodiment, the first Ig $C_H3$ domain binds Protein A and the second Ig $C_H3$ domain contains a mutation that reduces or abolishes Protein A binding such as an H95R modification (by IMGT exon numbering; H435R by EU numbering). The second $C_H3$ may further comprise a Y96F modification (by IMGT; Y436F by EU). Further modifications that may be found within the second $C_H3$ include: D16E, L18M, N44S, K52N, V57M, and V82I (by IMGT; D356E, L358M, N384S, K392N, V397M, and V422I by EU) in the case of IgG1 antibodies; N44S, K52N, and V82I (IMGT; N384S, K392N, and V422I by EU) in the case of IgG2 antibodies; and Q15R, N44S, K52N, V57M, R69K, E79Q, and V82I (by IMGT; Q355R, N384S, K392N, V397M, R409K, E419Q, and V422I by EU) in the case of IgG4 antibodies. Variations on the bispecific antibody format described above are contemplated within the scope disclosed herein.

Other exemplary bispecific formats that can be used in the context disclosed herein include, without limitation, e.g., scFv-based or diabody bispecific formats, IgG-scFv fusions, dual variable domain (DVD)-Ig, Quadroma, knobs-into-holes, common light chain (e.g., common light chain with knobs-into-holes, etc.), CrossMab, CrossFab, (SEED)body, leucine zipper, Duobody, IgG1/IgG2, dual acting Fab (DAF)-IgG, and Mab$^2$ bispecific formats (see, e.g., Klein et al. 2012, mAbs 4:6, 1-11, and references cited therein, for a review of the foregoing formats). Bispecific antibodies can also be constructed using peptide/nucleic acid conjugation, e.g., wherein unnatural amino acids with orthogonal chemical reactivity are used to generate site-specific antibody-oligonucleotide conjugates which then self-assemble into multimeric complexes with defined composition, valency and geometry. (See, e.g., Kazane et al., *J. Am. Chem. Soc.* [Epub: Dec. 4, 2012]).

Therapeutic Administration and Formulations

Provided herein are therapeutic compositions comprising the anti-influenza B HA antibodies or antigen-binding fragments thereof. Therapeutic compositions in accordance with the present disclosure will be administered with pharmaceutically acceptable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

The dose of antibody may vary depending upon the age and the size of a subject to be administered, target disease, conditions, route of administration, and the like. When an antibody disclosed herein is used for treating a disease or disorder in an adult patient, or for preventing such a disease, it is advantageous to administer the antibody disclosed herein normally at a single dose of about 0.1 to about 60 mg/kg body weight, or about 5 to about 60, about 10 to about 50, or about 20 to about 50 mg/kg body weight. Depending on the severity of the condition, the frequency and the duration of the treatment can be adjusted. In certain embodiments, the antibody or antigen-binding fragment thereof can be administered as an initial dose of at least about 0.1 mg to about 5000 mg, about 1 to about 2000 mg, about 5 to about 1000 mg, or about 10 to about 500 mg, to about 100 mg, or to about 50 mg. In certain embodiments, the initial dose may be followed by administration of a second or a plurality of subsequent doses of the antibody or antigen-binding fragment thereof in an amount that can be approximately the same or less than that of the initial dose, wherein the subsequent doses are separated by at least 1 day to 3 days; at least one week, at least 2 weeks; at least 3 weeks; at least 4 weeks; at least 5 weeks; at least 6 weeks; at least 7 weeks; at least 8 weeks; at least 9 weeks; at least 10 weeks; at least 12 weeks; or at least 14 weeks.

Various delivery systems are known and can be used to administer the pharmaceutical composition, e.g., encapsulation in liposomes, microparticles, microcapsules, recombinant cells capable of expressing the mutant viruses, receptor mediated endocytosis (see, e.g., Wu et al. (1987) J. Biol. Chem. 262:4429-4432). Methods of introduction include, but are not limited to, intradermal, transdermal, intramuscular, intraperitoneal, intravenous, subcutaneous, intranasal, epidural and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. The pharmaceutical composition can be also delivered in a vesicle, in particular a liposome (see, for example, Langer (1990) Science 249:1527-1533).

The use of nanoparticles to deliver the antibodies disclosed herein is also contemplated herein. Antibody-conjugated nanoparticles may be used both for therapeutic and diagnostic applications. Antibody-conjugated nanoparticles and methods of preparation and use are described in detail by Arruebo, M., et al. 2009 ("Antibody-conjugated nanoparticles for biomedical applications" in J. Nanomat. Volume 2009, Article ID 439389, 24 pages, doi: 10.1155/2009/439389), incorporated herein by reference. Nanoparticles may be developed and conjugated to antibodies contained in pharmaceutical compositions to target virally infected cells. Nanoparticles for drug delivery have also been described in, for example, U.S. Pat. No. 8,257,740, or U.S. Pat. No. 8,246,995, each incorporated herein in its entirety.

In certain situations, the pharmaceutical composition can be delivered in a controlled release system. In one embodiment, a pump may be used. In another embodiment, polymeric materials can be used. In yet another embodiment, a controlled release system can be placed in proximity of the composition's target, thus requiring only a fraction of the systemic dose.

The injectable preparations may include dosage forms for intravenous, subcutaneous, intracutaneous, intracranial, intraperitoneal and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is filled in an appropriate ampoule.

A pharmaceutical composition disclosed herein can be delivered subcutaneously or intravenously with a standard needle and syringe. In addition, with respect to subcutaneous delivery, a pen delivery device readily has applications in delivering a pharmaceutical composition disclosed herein. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition disclosed herein. Examples include, but certainly are not limited to AUTOPEN™ (Owen Mumford, Inc., Woodstock, UK), DISETRONIC™ pen (Disetronic Medical Systems, Burghdorf, Switzerland), HUMALOG MIX 75/25™ pen, HUMALOG™ pen, HUMALIN 70/30™ pen (Eli Lilly and Co., Indianapolis, Ind.), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPEN™, OPTIPEN PRO™, OPTIPEN STARLET™, and OPTICLIK™ (Sanofi-Aventis, Frankfurt, Germany), to name only a few. Examples of disposable pen delivery devices having applications in subcutaneous delivery of a pharmaceutical composition disclosed herein include, but certainly are not limited to the SOLOSTAR™ pen (Sanofi-Aventis), the FLEXPEN™ (Novo Nordisk), and the KWIKPEN™ (Eli Lilly), the SURECLICK™ Autoinjector (Amgen, Thousand Oaks, Calif.), the PENLET™ (Haselmeier, Stuttgart, Germany), the EPIPEN (Dey, L. P.) and the HUMIRA™ Pen (Abbott Labs, Abbott Park, Ill.), to name only a few.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the antibody contained is generally about 5 to about 5000 mg per dosage form in a unit dose; especially in the form of injection, it is preferred that the antibody is contained in about 5 to about 500 mg and in about 10 to about 250 mg for the other dosage forms.

Therapeutic Uses of the Antibodies

The antibodies disclosed herein are useful for the treatment, and/or prevention of a disease or disorder or condition associated with influenza B virus infection and/or for ameliorating at least one symptom associated with such disease, disorder or condition.

In certain embodiments, the antibodies provided herein are useful to treat subjects suffering from the severe and acute respiratory infection caused by influenza B virus. In some embodiments, the antibodies are useful in decreasing viral titers or reducing viral load in the host. In one embodiment, an antibody or antigen-binding fragment thereof may be administered at a therapeutic dose to a patient with influenza B virus infection.

One or more antibodies disclosed herein may be administered to relieve or prevent or decrease the severity of one or more of the symptoms or conditions of the disease or disorder, relative to an untreated but similarly situated subject. The antibodies may be used to ameliorate or reduce the severity of at least one symptom of influenza virus infection including, but not limited to fever, cough, sore throat, headache, body aches, fatigue, extreme exhaustion, shortness of breath, bronchitis, pneumonia, and death.

It is also contemplated herein to use one or more antibodies disclosed herein prophylactically to subjects at risk for developing an influenza virus infection such as immunocompromised individuals, elderly adults (65 years of age or older), children younger than 2 years of age, healthcare workers, family members in close proximity to a patient suffering from an influenza virus infection, and patients with a medical history (e.g., increased risk of pulmonary infection, heart disease or diabetes).

In a further embodiment the present antibodies are used for the preparation of a pharmaceutical composition for treating patients suffering from an influenza virus infection. In another embodiment, the antibodies are used as adjunct therapy with any other agent or any other therapy known to those skilled in the art useful for treating or ameliorating an influenza virus infection.

Combination Therapies

Combination therapies may include an anti-influenza B HA antibody and any additional therapeutic agent that may be advantageously combined with the antibody, or with a biologically active fragment of the antibody. The antibodies disclosed herein may be combined synergistically with one or more drugs or agents (e.g. anti-viral agents) used to treat influenza virus.

For example, exemplary anti-viral agents include, e.g., vaccines, neuraminidase inhibitors or nucleoside analogs. Other exemplary anti-viral agents that may be used in combination with an antibody provided herein can include, e.g., zidovudine, gangcyclovir, vidarabine, idoxuridine, trifluridine, foscarnet, acyclovir, ribavirin, amantadine, remantidine, saquinavir, indinavir, ritonavir, alpha-interferons and other interferons, a neuraminidase inhibitor (e.g., zanamivir (RELENZA®), oseltamivir (TAMIFLU®) laninamivir, peramivir), or rimantadine.

Other exemplary anti-viral drugs include, but are not limited to, a HA inhibitor, a sialic acid inhibitor and an M2 ion channel inhibitor. In one embodiment, the M2 ion channel inhibitor is amantadine or rimantadine.

In some embodiments, the antibodies provided herein may be combined with a second therapeutic agent to reduce the viral load in a patient with an influenza virus infection, or to ameliorate one or more symptoms of the infection.

The antibodies disclosed herein may be used in combination with an anti-inflammatory drug (e.g., corticosteroids, and non-steroidal anti-inflammatory drugs), a decongestant, an anti-histamine, an anti-infective drug, a different antibody to Influenza virus, an anti-viral drug, a vaccine for influenza virus, such as FLUMIST® or FLUVIRIN®, a dietary supplement such as anti-oxidants or another palliative therapy to treat an influenza virus infection. A palliative therapy includes treatment of the subject to make the subject more comfortable and/or to alleviate severity of symptoms of infection with influenza B.

In certain embodiments, the second therapeutic agent is another antibody to influenza. In certain embodiments, the second therapeutic agent is another antibody to influenza hemagglutinin (e.g., an influenza A hemagglutinin). In certain embodiments, the second therapeutic agent is another antibody to a different influenza protein, such as the neuraminidase, or the tetrameric ectodomain of matrix protein 2 (M2e protein). In certain embodiments, the second therapeutic agent is an antibody to a different protein such as the host transmembrane protease, serine 2 (TMPRSS2). The second antibody may be specific for one or more different influenza virus proteins from different subtypes or strains of the virus. It is contemplated herein to use a combination ("cocktail") of antibodies with broad neutralization or inhibitory activity against influenza virus. In some embodiments, non-competing antibodies may be combined and administered to a subject in need thereof, to reduce the ability of influenza virus to escape due to rapid mutation as a result of selection pressure. In some embodiments, the antibodies comprising the combination bind to distinct non-overlapping epitopes on the HA protein. The antibodies comprising the combination may block the virus attachment and/or entry into and/or fusion with host cells. The antibodies may interact with a hemagglutinin selected from any one or more of the influenza B strains and when used alone, or in combination with any one or more of the agents noted above, may neutralize any one or more of the influenza B strains including B/Victoria/2/87, B/Yamagata/16/88, B/Maryland/03/2008, B/Nanchang/3451/93, and/or B/Florida/4/2006.

It is also contemplated herein to use a combination of anti-influenza HA antibodies in addition to the anti-influenza B HA antibodies disclosed herein, wherein the combination comprises one or more antibodies that do not cross-compete; In some embodiments, the combination includes a first antibody with broad neutralization activity with a second antibody with activity against a narrow spectrum of isolates and that does not cross-compete with the first antibody.

As used herein, the term "in combination with" means that additional therapeutically active component(s) may be administered prior to, concurrent with, or after the administration of the anti-influenza B HA antibody disclosed herein. The term "in combination with" also includes sequential or concomitant administration of an anti-influenza-HA antibody and a second therapeutic agent.

The additional therapeutically active component(s) may be administered to a subject prior to administration of an anti-influenza B HA antibody disclosed herein. For example, a first component may be deemed to be administered "prior to" a second component if the first component is administered 1 week before, 72 hours before, 60 hours before, 48 hours before, 36 hours before, 24 hours before, 12 hours before, 6 hours before, 5 hours before, 4 hours before, 3 hours before, 2 hours before, 1 hour before, 30 minutes before, 15 minutes before, 10 minutes before, 5 minutes before, or less than 1 minute before administration of the second component. In other embodiments, the additional therapeutically active component(s) may be administered to a subject after administration of an anti-influenza B HA antibody disclosed herein. For example, a first component may be deemed to be administered "after" a second component if the first component is administered 1 minute after, 5 minutes after, 10 minutes after, 15 minutes after, 30 minutes after, 1 hour after, 2 hours after, 3 hours after, 4 hours after, 5 hours after, 6 hours after, 12 hours after, 24 hours after, 36 hours after, 48 hours after, 60 hours after, 72 hours after administration of the second component. In yet other embodiments, the additional therapeutically active component(s) may be administered to a subject concurrent with administration of an anti-influenza B HA antibody disclosed herein. "Concurrent" administration, for purposes of the present disclosure, includes, e.g., administration of an anti-influenza B HA antibody and an additional therapeutically active component to a subject in a single dosage form, or in separate dosage forms administered to the subject within about 30 minutes or less of each other. If administered in separate dosage forms, each dosage form may be administered via the same route (e.g., both the anti-influenza B HA antibody and the additional therapeutically active component may be administered intravenously, etc.); alternatively, each dosage form may be administered via a different route (e.g., the anti-influenza B HA antibody may be administered intravenously, and the additional therapeutically active component may be administered orally). In any event, administering the components in a single dosage from, in separate dosage forms by the same route, or in separate dosage forms by different routes are all considered "concurrent administration," for purposes of the present disclosure. For purposes of the present disclosure, administration of an anti-influenza B HA antibody "prior to", "concurrent with," or "after" (as those terms are defined herein above) administration of an additional therapeutically active component is considered administration of an anti-influenza B HA antibody "in combination with" an additional therapeutically active component.

The present disclosure includes pharmaceutical compositions in which an anti-influenza B HA antibody disclosed herein is co-formulated with one or more of the additional therapeutically active component(s) as described elsewhere herein.

Administration Regimens

According to certain embodiments, a single dose of an anti-influenza B HA antibody, or antigen-binding fragment thereof, provided herein (or a pharmaceutical composition comprising a combination of such an anti-influenza HA antibody or fragment and any of the additional therapeutically active agents mentioned herein) may be administered to a subject in need thereof. According to certain embodiments disclosed herein, multiple doses of an anti-influenza B HA antibody (or a pharmaceutical composition comprising a combination of an anti-influenza B HA antibody and any of the additional therapeutically active agents mentioned herein) may be administered to a subject over a defined time course. The methods according to this aspect of the disclosure comprise sequentially administering to a subject multiple doses of an anti-influenza B HA antibody. As used herein, "sequentially administering" means that each dose of anti-influenza B HA antibody is administered to the subject at a different point in time, e.g., on different days separated by a predetermined interval (e.g., hours, days, weeks or months). The present disclosure includes methods which comprise sequentially administering to the patient a single initial dose of an anti-influenza B HA antibody, followed by one or more secondary doses of the anti-influenza B HA antibody, and optionally followed by one or more tertiary doses of the anti-influenza B HA antibody.

The terms "initial dose," "secondary doses," and "tertiary doses," refer to the temporal sequence of administration of the anti-influenza B HA antibody. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses may all contain the same amount of anti-influenza-HA antibody, but generally may differ from one another in terms of frequency of administration. In certain embodiments, however, the amount of anti-influenza B HA antibody contained in the initial, secondary and/or tertiary doses varies from one another (e.g., adjusted up or down as appropriate) during the course of treatment. In certain embodiments, two or more (e.g., 2, 3, 4, or 5) doses are administered at the beginning of the treatment regimen as "loading doses" followed by subsequent doses that are administered on a less frequent basis (e.g., "maintenance doses").

In certain exemplary embodiments, each secondary and/or tertiary dose is administered 1 to 48 hours (e.g., 1, 1½, 2, 2½, 3, 3½, 4, 4½, 5, 5½, 6, 6½, 7, 7½, 8, 8½, 9, 9½, 10, 10½, 11, 11½, 12, 12½, 13, 13½, 14, 14½, 15, 15½, 16, 16½, 17, 17½, 18, 18½, 19, 19½, 20, 20½, 21, 21½, 22, 22½, 23, 23½, 24, 24½, 25, 25½, 26, 26½, or more) after the immediately preceding dose. The phrase "the immediately preceding dose," as used herein, means, in a sequence of multiple administrations, the dose of anti-influenza B HA antibody, which is administered to a patient prior to the administration of the very next dose in the sequence with no intervening doses.

The methods according to this aspect may comprise administering to a patient any number of secondary and/or tertiary doses of an anti-influenza B HA antibody. For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient.

In certain embodiments, the frequency at which the secondary and/or tertiary doses are administered to a patient can vary over the course of the treatment regimen. The frequency of administration may also be adjusted during the course of treatment by a physician depending on the needs of the individual patient following clinical examination.

Diagnostic Uses of the Antibodies

The anti-influenza B HA antibodies may be used to detect and/or measure influenza B HA in a sample, e.g., for diagnostic purposes. Some embodiments contemplate the use of one or more antibodies in assays to detect a disease or disorder such as viral infection. Exemplary diagnostic assays for influenza B HA may comprise, e.g., contacting a sample obtained from a patient, with an anti-influenza B HA antibody, wherein the anti-influenza B HA antibody is labeled with a detectable label or reporter molecule or used as a capture ligand to selectively isolate influenza B HA from patient samples. Alternatively, an unlabeled anti-influenza B HA antibody can be used in diagnostic applications in combination with a secondary antibody which is itself detectably labeled. The detectable label or reporter molecule can be a radioisotope, such as $^3$H, $^{14}$C, $^{32}$P, $^{35}$S, or $^{125}$I; a fluorescent or chemiluminescent moiety such as fluorescein isothiocyanate, or rhodamine; or an enzyme such as alkaline phosphatase, β-galactosidase, horseradish peroxidase, or luciferase. Specific exemplary assays that can be used to detect or measure influenza B HA in a sample include enzyme-linked immunosorbent assay (ELISA), radioimmunoassay (RIA), and fluorescence-activated cell sorting (FACS).

Samples that can be used in influenza B HA diagnostic assays include any tissue or fluid sample obtainable from a patient, which contains detectable quantities of either influenza B HA, or fragments thereof, under normal or pathological conditions. Generally, levels of influenza B HA in a particular sample obtained from a healthy patient (e.g., a patient not afflicted with a disease associated with influenza will be measured to initially establish a baseline, or standard, level of influenza B HA. This baseline level of influenza B HA can then be compared against the levels of influenza B HA measured in samples obtained from individuals suspected of having an influenza B HA-associated condition, or symptoms associated with such condition.

The antibodies specific for influenza B HA may contain no additional labels or moieties, or they may contain an N-terminal or C-terminal label or moiety. In one embodiment, the label or moiety is biotin. In a binding assay, the location of a label (if any) may determine the orientation of the peptide relative to the surface upon which the peptide is bound. For example, if a surface is coated with avidin, a peptide containing an N-terminal biotin will be oriented such that the C-terminal portion of the peptide will be distal to the surface.

EXAMPLES

The following examples are put forth so as to provide those of ordinary skill in the art with a complete disclosure and description of how to make and use the methods and compositions disclosed herein, and are not intended to limit the scope of what the inventors regard as their disclosure. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, room temperature is about 25° C., and pressure is at or near atmospheric.

Example 1: Generation of Human Antibodies to Influenza B Hemagglutinin (HA)

Human antibodies to influenza hemagglutinin were generated in a VELOCIMMUNE® mouse comprising DNA encoding human immunoglobulin heavy and kappa light chain variable regions. The mice were immunized with a combination of vectors expressing influenza A and B hemagglutinins, followed by infection and recovery with influenza A and B strains, followed by a booster comprising a mixture of recombinant hemagglutinin proteins. The antibody immune response was monitored by an influenza HA specific immunoassay. Anti-influenza B HA antibodies were isolated directly from antigen-positive mouse B cells without fusion to myeloma cells, as described in U.S. Pat. No. 7,582,298, herein specifically incorporated by reference in its entirety. Using this method, fully human anti-influenza HA antibodies (i.e., antibodies possessing human variable domains and human constant domains) were obtained.

An exemplary antibody described herein is designated mAb 35490. The biological properties of the exemplary antibody generated in accordance with the methods of this Example are described in detail in the Examples set forth below.

Example 2: Heavy and Light Chain Variable Region Amino Acid and Nucleotide Sequences Table 1 sets forth the amino acid sequence identifiers of the heavy and light chain variable regions and CDRs, as well as the heavy chain and light chain sequences, of an exemplary anti-influenza B HA antibody. The corresponding nucleic acid sequence identifiers are set forth in Table 2.

TABLE 1

Amino Acid Sequence Identifiers

| Antibody Designation | SEQ ID NOs: | | | | | | | | | |
|---|---|---|---|---|---|---|---|---|---|---|
| | HCVR | HCDR1 | HCDR2 | HCDR3 | LCVR | LCDR1 | LCDR2 | LCDR3 | HC | LC |
| mAb35490 | 2 | 4 | 6 | 8 | 10 | 12 | 14 | 16 | 18 | 20 |

TABLE 2

Nucleic Acid Sequence Identifiers

| Antibody Designation | SEQ ID NOs: | | | | | | | | | |
|---|---|---|---|---|---|---|---|---|---|---|
| | HCVR | HCDR1 | HCDR2 | HCDR3 | LCVR | LCDR1 | LCDR2 | LCDR3 | HC | LC |
| mAb35490 | 1 | 3 | 5 | 7 | 9 | 11 | 13 | 15 | 17 | 19 |

Antibodies disclosed herein have fully human variable regions but can have mouse constant regions (e.g., a mouse IgG1 Fc or a mouse IgG2 Fc (a or b isotype)) or human constant regions (e.g., a human IgG1 Fc or a human IgG4 Fc). As will be appreciated by a person of ordinary skill in the art, an antibody having a particular Fc isotype can be converted to an antibody with a different Fc isotype (e.g., an antibody with a mouse IgG1 Fc can be converted to an antibody with a human IgG4, etc.), but in any event, the variable domains (including the CDRs)—which are indicated by the numerical identifiers shown in Tables 1 and 2 will remain the same, and the binding properties to antigen are expected to be identical or substantially similar regardless of the nature of the Fc domain.

Example 3: Anti-Hemagglutinin Antibody Binding to Influenza-Infected Cells

MDCK London cells were seeded at 40,000 cells/well in 50 µL of infection media (DMEM containing 1% sodium pyruvate, 0.21% Low IgG BSA solution, and 0.5% Gentamicin) in a 96-well plate. The cells were incubated at 37° C. with 5% $CO_2$ for four hours. Plates were then infected with 50 µL of Influenza B/Florida/4/2006 virus (a vaccine strain of B/Yamagata lineage) at a dilution of 10E-2.5, tapped gently and placed back at 37° C. 5% $CO_2$ for 20 hours. Plates were then washed once with PBS and fixed with 50 µL of 4% PFA in PBS and incubated for 15 minutes at room temperature. Plates were washed three times with PBS and blocked with 300 µL of StartingBlock™ (PBS) Blocking Buffer (Thermo Fisher Scientific) for one hour at room temperature. Influenza B anti-HA antibody mAb35490P (formatted with a human IgG1 Fc) and a human IgG1 isotype control antibody were diluted to a starting concentration of 100 µg/mL in Blocking Buffer and titrated 1:4 to a final concentration of 6.1E-3 µg/mL. After incubation, Blocking Buffer was removed from plates and diluted antibodies were added onto cells at 75 µL/well. Plates were incubated for one hour at room temperature. Following incubation, plates were washed three times with Wash Buffer (imidazole-buffered saline and Tween® 20 diluted to 1× in Milli-Q water) and overlayed with 75 µL/well of a secondary antibody (Peroxidase AffiniPure Donkey anti-Human IgG, Jackson ImmunoResearch) diluted 1:2000 in Blocking Buffer. Secondary solution was incubated on plates for one hour at room temperature. Subsequently, plates were washed three times with Wash Buffer, and 75 µL/well of developing substrate ELISA Pico substrate (prepared 1:1) was added. Plates were read immediately for luminescence on a Molecular Devices Spectramax i3x plate reader, and the $EC_{50}$ data are shown in Table 3.

TABLE 3

| FluB Infected Cell Anti-HA Binding ELISA | |
|---|---|
| Antibody | $EC_{50}$ log[M] |
| Human IqG1 isotype control | No Binding |
| mAb35490 | 7.610E-10 |

As seen in Table 3, mAb35490 bound to Influenza B infected cells at a sub-nM concentration, demonstrating specific binding to HA.

Example 4: Prevention of Influenza B-Induced Mortality Via Prophylactic Antibody Administering Balb/C Elite mice were treated with 5 mg/kg or 0.5 mg/kg of mAb35490 (formatted with a human IgG1 Fc) or 5 mg/kg of a human IgG1 isotype control antibody diluted in PBS via subcutaneous injection into the neck scruff five days prior to infection. On the day of infection, the Influenza B/Florida/4/2006 virus stock was thawed on ice and diluted in PBS from a stock of 2.05E08 pfu/mL to contain 4000 pfu virus in 20 µL PBS (2.0E05 pfu/mL). The virus was kept on ice at all times. Each mouse was injected with a cocktail of 2.4 mg/kg Ketamine and 0.1 mg/kg Xylazine, and allowed to rest for approximately 10-15 minutes until they were fully asleep. Each mouse was then intranasally dosed with 20 µL of the virus (4000 pfu) to fully inhale the virus. The mice were then monitored for weight loss and morbidity for two weeks following infection. Weight loss of 25% or greater from the initial weight at the time of infection resulted in euthanization. Results are shown in Table 4.

TABLE 4

Mouse survival after administration of mAb35490 or an isotype control

| Antibody | Dose (mg/kg) | Survival % (2 weeks post-infection) |
|---|---|---|
| mAb35490 | 5 | 100 |
| mAb35490 | 0.5 | 100 |
| Human IgG1 isotype control | 5 | 0 (euthanized 8 days post-infection) |

All animals treated with the human IgG1 isotype control antibody succumbed to the infection and needed to be euthanized by eight days post-infection. All animals treated with both 5 mg/kg and 0.5 mg/kg mAb35490 survived the infection, demonstrating efficacy of the FluB anti-HA antibody mAb35490.

What is claimed is:

1. An isolated recombinant antibody or antigen-binding fragment thereof that specifically binds to influenza B hemagglutinin (HA), wherein the antibody comprises (i) three heavy chain complementarity determining regions (CDRs) (HCDR1, HCDR2, and HCDR3) contained within a heavy chain variable region (HCVR) comprising the amino acid sequence set forth in SEQ ID NO: 2; and (ii) three light chain CDRs (LCDR1, LCDR2, and LCDR3) contained within a light chain variable region (LCVR) comprising the amino acid sequence set forth in SEQ ID NO: 10.

2. The isolated antibody or antigen-binding fragment thereof of claim 1, comprising an HCVR having an amino acid sequence of SEQ ID NO: 2.

3. The isolated antibody or antigen-binding fragment thereof of claim 1, comprising an LCVR having an amino acid sequence of SEQ ID NO: 10.

4. An isolated antibody or antigen-binding fragment thereof, comprising:
- (a) an HCDR1 domain having an amino acid sequence of SEQ ID NO: 4;
- (b) an HCDR2 domain having an amino acid sequence of SEQ ID NO: 6;
- (c) an HCDR3 domain having an amino acid sequence of SEQ ID NO: 8;
- (d) an LCDR1 domain having an amino acid sequence of SEQ ID NO: 12;
- (e) an LCDR2 domain having an amino acid sequence of SEQ ID NO: 14; and
- (f) an LCDR3 domain having an amino acid sequence of SEQ ID NO: 16.

5. The isolated antibody or antigen-binding fragment thereof of claim 4, wherein said isolated antibody or antigen-binding fragment thereof specifically binds to influenza B hemagglutinin (HA).

6. The isolated antibody or antigen-binding fragment thereof of claim 4, which is an antibody comprising an HCVR having an amino acid sequence of SEQ ID NO: 2.

7. The isolated antibody or antigen-binding fragment thereof of claim 4, which is an antibody comprising an LCVR having an amino acid sequence of SEQ ID NO: 10.

8. The isolated antibody or antigen-binding fragment thereof of claim 1, comprising an HCVR/LCVR amino acid sequence pair of SEQ ID NOs: 2/10.

9. The isolated antibody or antigen-binding fragment thereof of claim 1 which is an IgG1 antibody.

10. The isolated antibody or antigen-binding fragment thereof of claim 1 which is an IgG4 antibody.

11. The isolated antibody or antigen-binding fragment thereof of claim 1 which is a bispecific antibody.

12. A pharmaceutical composition comprising the isolated antibody or antigen-binding fragment thereof of claim 1 and a pharmaceutically acceptable carrier or diluent.

13. The pharmaceutical composition of claim 12, wherein said pharmaceutical composition further comprises a second therapeutic agent.

14. The pharmaceutical composition of claim 13, wherein said second therapeutic agent is selected from the group consisting of: an anti-viral drug, an anti-inflammatory drug, a different antibody that binds specifically to influenza HA, a vaccine for influenza, a dietary supplement, and another palliative therapy to treat an influenza infection.

15. The pharmaceutical composition of claim 14, wherein said anti-inflammatory drug is selected from the group consisting of corticosteroids and non-steroidal anti-inflammatory drugs.

16. The pharmaceutical composition of claim 14, wherein said dietary supplement is an anti-oxidant.

17. The pharmaceutical composition of claim 14, wherein said anti-viral drug is oseltamivir.

18. The pharmaceutical composition of claim 14, wherein said anti-viral drug is an anti-influenza A drug.

19. The pharmaceutical composition of claim 18, wherein said anti-influenza A drug is an antibody.

20. The pharmaceutical composition of claim 19, wherein said antibody binds specifically to influenza A HA.

21. The isolated antibody or antigen-binding fragment thereof of claim 1, wherein said antibody or fragment has one or more of the following characteristics:
- (a) binds to influenza B HA with an $EC_{50}$ of less than about $10^{-9}$ M; and
- (b) demonstrates an increase in survival in an influenza B-infected animal after administration to said influenza B-infected animal, as compared to a comparable influenza B-infected animal without said administration.

* * * * *

SEQUENCE LISTING

<160> NUMBER OF SEQ ID NOS: 24

<210> SEQ ID NO 1
<211> LENGTH: 351
<212> TYPE: DNA
<213> ORGANISM: Artificial Sequence
<220> FEATURE:
<223> OTHER INFORMATION: synthetic

<400> SEQUENCE: 1

```
gaggtgcagc tggtggagtc tggaggagac ttggtccagc ctgggggtc cctgagactc    60
tcctgtgcag cctctggatt caccgtcagt agcaactata tgagttgggt ccgccaggtt   120
ccagggaagg ggctggactg ggtctcagtt acttatagcg gtggtaacac atactacgca   180
gactccgtga aggccgatt caccatttcc agacacaatt ccaagaacac gctatatctt   240
caaatgaaca gcctgagaat tgaggacacg gccgtttatt actgtgcgac cgtacccctcg   300
tttcacggta tggacgtctg gggccaaggg accacggtca ccgtctcctc a             351
```

<210> SEQ ID NO 2
<211> LENGTH: 117
<212> TYPE: PRT
<213> ORGANISM: Artificial Sequence
<220> FEATURE:
<223> OTHER INFORMATION: synthetic

<400> SEQUENCE: 2

```
Glu Val Gln Leu Val Glu Ser Gly Gly Asp Leu Val Gln Pro Gly Gly
1               5                   10                  15
Ser Leu Arg Leu Ser Cys Ala Ala Ser Gly Phe Thr Val Ser Ser Asn
            20                  25                  30
Tyr Met Ser Trp Val Arg Gln Val Pro Gly Lys Gly Leu Asp Trp Val
        35                  40                  45
Ser Val Thr Tyr Ser Gly Gly Asn Thr Tyr Tyr Ala Asp Ser Val Lys
    50                  55                  60
Gly Arg Phe Thr Ile Ser Arg His Asn Ser Lys Asn Thr Leu Tyr Leu
65                  70                  75                  80
Gln Met Asn Ser Leu Arg Ile Glu Asp Thr Ala Val Tyr Tyr Cys Ala
                85                  90                  95
Thr Val Pro Ser Phe His Gly Met Asp Val Trp Gly Gln Gly Thr Thr
            100                 105                 110
Val Thr Val Ser Ser
        115
```

<210> SEQ ID NO 3
<211> LENGTH: 24
<212> TYPE: DNA
<213> ORGANISM: Artificial Sequence
<220> FEATURE:
<223> OTHER INFORMATION: synthetic

<400> SEQUENCE: 3

```
ggattcaccg tcagtagcaa ctat                                            24
```

<210> SEQ ID NO 4
<211> LENGTH: 8
<212> TYPE: PRT

```
<213> ORGANISM: Artificial Sequence
<220> FEATURE:
<223> OTHER INFORMATION: synthetic

<400> SEQUENCE: 4

Gly Phe Thr Val Ser Ser Asn Tyr
1               5

<210> SEQ ID NO 5
<211> LENGTH: 21
<212> TYPE: DNA
<213> ORGANISM: Artificial Sequence
<220> FEATURE:
<223> OTHER INFORMATION: synthetic

<400> SEQUENCE: 5
acttatagcg gtggtaacac a                                                   21

<210> SEQ ID NO 6
<211> LENGTH: 7
<212> TYPE: PRT
<213> ORGANISM: Artificial Sequence
<220> FEATURE:
<223> OTHER INFORMATION: synthetic

<400> SEQUENCE: 6

Thr Tyr Ser Gly Gly Asn Thr
1               5

<210> SEQ ID NO 7
<211> LENGTH: 33
<212> TYPE: DNA
<213> ORGANISM: Artificial Sequence
<220> FEATURE:
<223> OTHER INFORMATION: synthetic

<400> SEQUENCE: 7
gcgaccgtac cctcgtttca cggtatggac gtc                                      33

<210> SEQ ID NO 8
<211> LENGTH: 11
<212> TYPE: PRT
<213> ORGANISM: Artificial Sequence
<220> FEATURE:
<223> OTHER INFORMATION: synthetic

<400> SEQUENCE: 8

Ala Thr Val Pro Ser Phe His Gly Met Asp Val
1               5                   10

<210> SEQ ID NO 9
<211> LENGTH: 324
<212> TYPE: DNA
<213> ORGANISM: Artificial Sequence
<220> FEATURE:
<223> OTHER INFORMATION: synthetic

<400> SEQUENCE: 9
gacatccaga tgacccagtc tccatcctcc ctgtctgcat ctgtaggaga cagagtcacc         60
atcacttgcc gggcaagtca gagcattagc agctatttaa attggtatca gcagaaacca        120
gggaaagccc ctaagctcct gatctatgct gcatccagtt tgcaaagtgg ggtcccgtca        180
aggttcagtg gcagtggatc tgggacagat ttcactctca ccatcagcag tctgcaacct        240
gaagattttg caacttacta ctgtcaacag agttacagta cccctccgat caccttcggc        300
```
caagggacac gactggagat taaa                                          324

<210> SEQ ID NO 10
<211> LENGTH: 108
<212> TYPE: PRT
<213> ORGANISM: Artificial Sequence
<220> FEATURE:
<223> OTHER INFORMATION: synthetic

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys
            100                 105

<210> SEQ ID NO 11
<211> LENGTH: 18
<212> TYPE: DNA
<213> ORGANISM: Artificial Sequence
<220> FEATURE:
<223> OTHER INFORMATION: synthetic

<400> SEQUENCE: 11
cagagcatta gcagctat                                                 18

<210> SEQ ID NO 12
<211> LENGTH: 6
<212> TYPE: PRT
<213> ORGANISM: Artificial Sequence
<220> FEATURE:
<223> OTHER INFORMATION: synthetic

<400> SEQUENCE: 12

Gln Ser Ile Ser Ser Tyr
1               5

<210> SEQ ID NO 13
<211> LENGTH: 9
<212> TYPE: DNA
<213> ORGANISM: Artificial Sequence
<220> FEATURE:
<223> OTHER INFORMATION: synthetic

<400> SEQUENCE: 13 gctgcatcc                                                            9

<210> SEQ ID NO 14
<211> LENGTH: 3
<212> TYPE: PRT
<213> ORGANISM: Artificial Sequence
<220> FEATURE:
<223> OTHER INFORMATION: synthetic

<400> SEQUENCE: 14

Ala Ala Ser
1

<210> SEQ ID NO 15
<211> LENGTH: 30
<212> TYPE: DNA
<213> ORGANISM: Artificial Sequence
<220> FEATURE:
<223> OTHER INFORMATION: synthetic

<400> SEQUENCE: 15
caacagagtt acagtaccccc tccgatcacc                                     30

<210> SEQ ID NO 16
<211> LENGTH: 10
<212> TYPE: PRT
<213> ORGANISM: Artificial Sequence
<220> FEATURE:
<223> OTHER INFORMATION: synthetic

<400> SEQUENCE: 16

Gln Gln Ser Tyr Ser Thr Pro Pro Ile Thr
1               5                   10

<210> SEQ ID NO 17
<211> LENGTH: 1344
<212> TYPE: DNA
<213> ORGANISM: Artificial Sequence
<220> FEATURE:
<223> OTHER INFORMATION: synthetic

<400> SEQUENCE: 17
gaggtgcagc tggtggagtc tggaggagac ttggtccagc ctgggggtc cctgagactc      60 tcctgtgcag cctctggatt caccgtcagt agcaactata tgagttgggt ccgccaggtt    120
ccagggaagg ggctgactg gtctcagtt acttatagcg gtggtaacac atactacgca      180
gactccgtga aaggccgatt caccatttcc agacacaatt ccaagaacac gctatatctt    240
caaatgaaca gcctgagaat tgaggacacg gccgtttatt actgtgcgac cgtaccctcg    300
tttcacggta tggacgtctg ggggccaaggg accacggtca ccgtctcctc agcctccacc    360
aagggcccat cggtcttccc cctggcaccc tcctccaaga gcacctctgg gggcacagcg    420
gccctgggct gcctggtcaa ggactacttc cccgaaccgg tgacggtgtc gtggaactca    480
ggcgccctga ccagcggcgt gcacaccttc ccggctgtcc tacagtcctc aggactctac    540
tccctcagca gcgtggtgac cgtgccctcc agcagcttgg gcacccagac ctacatctgc    600
aacgtgaatc acaagcccag caacaccaag gtggacaaga agttgagcc caaatcttgt    660 gacaaaactc acacatgccc accgtgccca gcacctgaac tcctgggggg accgtcagtc    720
ttcctcttcc ccccaaaacc caaggacacc ctcatgatct cccggacccc tgaggtcaca    780
tgcgtggtgg tggacgtgag ccacgaagac cctgaggtca agttcaactg gtacgtggac    840
ggcgtggagg tgcataatgc caagacaaag ccgcgggagg agcagtacaa cagcacgtac    900
cgtgtggtca gcgtcctcac cgtcctgcac caggactggc tgaatggcaa ggagtacaag    960
tgcaaggtct ccaacaaagc cctcccagcc ccatcgaga aaaccatctc caaagccaaa    1020
gggcagcccc gagaaccaca ggtgtacacc ctgccccat cccgggatga gctgaccaag    1080
aaccaggtca gcctgacctg cctggtcaaa ggcttctatc ccagcgacat cgccgtggag    1140
tgggagagca atgggcagcc ggagaacaac tacaagacca cgcctcccgt gctggactcc    1200

```
gacggctcct tcttcctcta cagcaagctc accgtggaca agagcaggtg gcagcagggg    1260
aacgtcttct catgctccgt gatgcatgag gctctgcaca accactacac gcagaagtcc    1320
ctctccctgt ctccgggtaa atga                                          1344
```

<210> SEQ ID NO 18
<211> LENGTH: 447
<212> TYPE: PRT
<213> ORGANISM: Artificial Sequence
<220> FEATURE:
<223> OTHER INFORMATION: synthetic

<400> SEQUENCE: 18

```
Glu Val Gln Leu Val Glu Ser Gly Gly Asp Leu Val Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Val Pro Gly Lys Gly Leu Asp Trp Val
        35                  40                  45

Ser Val Thr Tyr Ser Gly Gly Asn Thr Tyr Ala Asp Ser Val Lys
    50                  55                  60

Gly Arg Phe Thr Ile Ser Arg His Asn Ser Lys Asn Thr Leu Tyr Leu
65                  70                  75                  80

Gln Met Asn Ser Leu Arg Ile Glu Asp Thr Ala Val Tyr Tyr Cys Ala
                85                  90                  95

Thr Val Pro Ser Phe His Gly Met Asp Val Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335
```

```
Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 19
<211> LENGTH: 648
<212> TYPE: DNA
<213> ORGANISM: Artificial Sequence
<220> FEATURE:
<223> OTHER INFORMATION: synthetic

<400> SEQUENCE: 19
gacatccaga tgacccagtc tccatcctcc ctgtctgcat ctgtaggaga cagagtcacc      60
atcacttgcc gggcaagtca gagcattagc agctatttaa attggtatca gcagaaacca     120
gggaaagccc ctaagctcct gatctatgct gcatccagtt tgcaaagtgg ggtcccgtca     180
aggttcagtg gcagtggatc tgggacagat ttcactctca ccatcagcag tctgcaacct     240
gaagattttg caacttacta ctgtcaacag agttacagta cccctccgat caccttcggc     300
caagggacac gactggagat taaacgaact gtggctgcac catctgtctt catcttcccg     360
ccatctgatg agcagttgaa atctggaact gcctctgttg tgtgcctgct gaataacttc     420
tatcccagag aggccaaagt acagtggaag gtggataacg ccctccaatc gggtaactcc     480
caggagagtg tcacagagca ggacagcaag gacagcacct acagcctcag cagcaccctg     540
acgctgagca aagcagacta cgagaaacac aaagtctacg cctgcgaagt cacccatcag     600
ggcctgagct cgcccgtcac aaagagcttc aacaggggag agtgttag                  648

<210> SEQ ID NO 20
<211> LENGTH: 215
<212> TYPE: PRT
<213> ORGANISM: Artificial Sequence
<220> FEATURE:
<223> OTHER INFORMATION: synthetic

<400> SEQUENCE: 20

Asp Ile Gln Met Thr Gln Ser Pro Ser Ser Leu Ser Ala Ser Val Gly
1               5                  10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
```

```
            85                  90                  95
Ile Thr Phe Gly Gln Gly Thr Arg Leu Glu Ile Lys Arg Thr Val Ala
            100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
        130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
        210                 215

<210> SEQ ID NO 21
<211> LENGTH: 585
<212> TYPE: PRT
<213> ORGANISM: Artificial Sequence
<220> FEATURE:
<223> OTHER INFORMATION: AAA43697.1 HA from B/Victoria/2/87

<400> SEQUENCE: 21

Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Thr
        35                  40                  45

Thr Thr Pro Thr Lys Ser His Phe Ala Asn Leu Lys Gly Thr Lys Thr
    50                  55                  60

Arg Gly Lys Leu Cys Pro Lys Cys Leu Asn Cys Thr Asp Leu Asp Val
65                  70                  75                  80

Ala Leu Ala Arg Pro Lys Cys Met Gly Thr Ile Pro Ser Ala Lys Ala
                85                  90                  95

Ser Ile Leu His Glu Val Lys Pro Val Thr Ser Gly Cys Phe Pro Ile
            100                 105                 110

Met His Asp Arg Thr Lys Ile Arg Gln Leu Pro Asn Leu Leu Arg Gly
        115                 120                 125

Tyr Glu His Ile Arg Leu Ser Thr His Asn Val Ile Asn Ala Glu Thr
    130                 135                 140

Ala Pro Gly Gly Pro Tyr Lys Val Gly Thr Ser Gly Ser Cys Pro Asn
145                 150                 155                 160

Val Thr Asn Gly Asn Gly Phe Phe Ala Thr Met Ala Trp Ala Val Pro
                165                 170                 175

Lys Asn Asp Asn Asn Lys Thr Ala Thr Asn Pro Leu Thr Val Glu Val
            180                 185                 190

Pro Tyr Ile Cys Thr Glu Gly Glu Asp Gln Ile Thr Val Trp Gly Phe
        195                 200                 205

His Ser Asp Ser Glu Thr Gln Met Val Lys Leu Tyr Gly Asp Ser Lys
    210                 215                 220

Pro Gln Lys Phe Thr Ser Ser Ala Asn Gly Val Thr Thr His Tyr Val
```

```
                225                 230                 235                 240
Ser Gln Ile Gly Gly Phe Pro Asn Gln Ala Glu Asp Gly Gly Leu Pro
                245                 250                 255

Gln Ser Gly Arg Ile Val Val Asp Tyr Met Val Gln Lys Ser Gly Lys
            260                 265                 270

Thr Gly Thr Ile Thr Tyr Gln Arg Gly Ile Leu Leu Pro Gln Lys Val
        275                 280                 285

Trp Cys Ala Ser Gly Arg Ser Lys Val Ile Lys Gly Ser Leu Pro Leu
    290                 295                 300

Ile Gly Glu Ala Asp Cys Leu His Glu Lys Tyr Gly Gly Leu Asn Lys
305                 310                 315                 320

Ser Lys Pro Tyr Tyr Thr Gly Glu His Ala Lys Ala Ile Gly Asn Cys
                325                 330                 335

Pro Ile Trp Val Lys Thr Pro Leu Lys Leu Ala Asn Gly Thr Lys Tyr
            340                 345                 350

Arg Pro Pro Ala Lys Leu Leu Lys Glu Arg Gly Phe Phe Gly Ala Ile
        355                 360                 365

Ala Gly Phe Leu Glu Gly Gly Trp Glu Gly Met Ile Ala Gly Trp His
    370                 375                 380

Gly Tyr Thr Ser His Gly Ala His Gly Val Ala Val Ala Ala Asp Leu
385                 390                 395                 400

Lys Ser Thr Gln Glu Ala Ile Asn Lys Ile Thr Lys Asn Leu Asn Ser
                405                 410                 415

Leu Ser Glu Leu Glu Val Lys Asn Leu Gln Arg Leu Ser Gly Ala Met
            420                 425                 430

Asp Glu Leu His Asn Glu Ile Leu Glu Leu Asp Glu Lys Val Asp Asp
        435                 440                 445

Leu Arg Ala Asp Thr Ile Ser Ser Gln Ile Glu Leu Ala Val Leu Leu
    450                 455                 460

Ser Asn Glu Gly Ile Ile Asn Ser Glu Asp Glu His Leu Leu Ala Leu
465                 470                 475                 480

Glu Arg Lys Leu Lys Lys Met Leu Gly Pro Ser Ala Val Glu Ile Gly
                485                 490                 495

Asn Gly Cys Phe Glu Thr Lys His Lys Cys Asn Gln Thr Cys Leu Asp
            500                 505                 510

Arg Ile Ala Ala Gly Thr Phe Asn Ala Gly Glu Phe Ser Leu Pro Thr
        515                 520                 525

Phe Asp Ser Leu Asn Ile Thr Ala Ala Ser Leu Asn Asp Asp Gly Leu
    530                 535                 540

Asp Asn His Thr Ile Leu Leu Tyr Tyr Ser Thr Ala Ala Ser Ser Leu
545                 550                 555                 560

Ala Val Thr Leu Met Ile Ala Ile Phe Ile Val Tyr Met Val Ser Arg
                565                 570                 575

Asp Asn Val Ser Cys Ser Ile Cys Leu
            580                 585

<210> SEQ ID NO 22
<211> LENGTH: 346
<212> TYPE: PRT
<213> ORGANISM: Artificial Sequence
<220> FEATURE:
<223> OTHER INFORMATION: AAD02807.1 HA from B/Nanchang/3451/93

<400> SEQUENCE: 22

Asp Arg Ile Cys Thr Gly Ile Thr Ser Ser Asn Ser Pro His Val Val
```

-continued

```
                1               5                  10                 15
            Lys Thr Ala Thr Gln Gly Glu Val Asn Val Thr Gly Val Ile Pro Leu
                            20                  25                  30

Thr Thr Thr Pro Thr Lys Ser His Phe Ala Asn Leu Lys Gly Thr Lys
                            35                  40                  45

Thr Arg Gly Lys Leu Cys Pro Asn Cys Leu Asn Cys Thr Asp Leu Asp
                        50                  55                  60

Val Ala Leu Gly Arg Pro Met Cys Val Gly Thr Thr Pro Ser Ala Lys
             65                 70                  75                  80

Ala Ser Ile Leu His Glu Val Arg Pro Val Thr Ser Gly Cys Phe Pro
                                85                  90                  95

Ile Met His Asp Arg Thr Lys Ile Arg Gln Leu Pro Asn Leu Leu Arg
                            100                 105                 110

Gly Tyr Glu Asn Ile Arg Leu Ser Thr Gln Asn Val Ile Asn Ala Glu
                        115                 120                 125

Lys Ala Pro Gly Gly Pro Tyr Arg Leu Gly Thr Ser Gly Ser Cys Pro
            130                 135                 140

Asn Ala Thr Ser Arg Ser Gly Phe Phe Ala Thr Met Ala Trp Ala Val
            145                 150                 155                 160

Pro Gly Asp Asn Asn Lys Thr Ala Thr Gly Pro Leu Thr Val Glu Val
                            165                 170                 175

Pro Tyr Ile Cys Thr Lys Gly Glu Asp Gln Ile Thr Val Trp Gly Phe
                        180                 185                 190

His Ser Asp Ser Lys Thr Arg Met Arg Ser Leu Tyr Gly Asp Ser Asn
                    195                 200                 205

Pro Gln Lys Phe Thr Ser Ser Ala Asn Gly Val Thr Thr His Tyr Val
            210                 215                 220

Ser Gln Ile Gly Gly Phe Pro Asp Gln Thr Glu Asp Gly Gly Leu Pro
            225                 230                 235                 240

Gln Ser Gly Arg Ile Val Val Asp Tyr Met Val Gln Lys Pro Gly Lys
                            245                 250                 255

Thr Gly Thr Ile Val Tyr Gln Arg Gly Val Leu Leu Pro Gln Lys Val
                        260                 265                 270

Trp Cys Ala Ser Gly Arg Ser Lys Val Ile Lys Gly Ser Leu Pro Leu
                    275                 280                 285

Ile Gly Glu Ala Asp Cys Leu His Glu Lys Tyr Gly Gly Leu Asn Lys
                290                 295                 300

Ser Lys Pro Tyr Tyr Thr Gly Glu His Ala Lys Ala Ile Gly Asn Cys
            305                 310                 315                 320

Pro Ile Trp Val Lys Thr Pro Leu Lys Leu Ala Asn Gly Thr Lys Tyr
                            325                 330                 335

Arg Pro Pro Ala Lys Leu Leu Lys Glu Arg
                        340                 345

<210> SEQ ID NO 23
<211> LENGTH: 584
<212> TYPE: PRT
<213> ORGANISM: Artificial Sequence
<220> FEATURE:
<223> OTHER INFORMATION: ABN50712.1 HA from B/Singapore/11/1994

<400> SEQUENCE: 23

Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
```

```
                20                  25                  30
Thr Ala Thr Gln Gly Glu Val Asn Val Thr Gly Val Ile Pro Leu Thr
            35                  40                  45
Thr Thr Pro Thr Lys Ser His Phe Ala Asn Leu Lys Gly Thr Lys Thr
 50                  55                  60
Arg Gly Lys Leu Cys Pro Asn Cys Leu Asn Cys Thr Asp Leu Asp Val
 65                  70                  75                  80
Ala Leu Gly Arg Pro Met Cys Val Gly Thr Thr Pro Ser Ala Lys Ala
                85                  90                  95
Ser Ile Leu His Glu Val Arg Pro Val Thr Ser Gly Cys Phe Pro Ile
            100                 105                 110
Met His Asp Arg Thr Lys Ile Arg Gln Leu Pro Asn Leu Leu Arg Gly
        115                 120                 125
Tyr Glu Asn Ile Arg Leu Ser Thr Gln Asn Val Ile Asn Ala Glu Lys
    130                 135                 140
Ala Pro Gly Gly Pro Tyr Arg Leu Gly Thr Ser Gly Ser Cys Pro Asn
145                 150                 155                 160
Ala Thr Ser Arg Ser Gly Phe Phe Ala Thr Met Ala Trp Ala Val Pro
                165                 170                 175
Arg Asp Asn Asn Lys Thr Ala Thr Asn Pro Leu Thr Val Glu Val Pro
            180                 185                 190
Tyr Val Cys Thr Glu Gly Glu Asp Gln Ile Thr Val Trp Gly Phe His
        195                 200                 205
Ser Asp Asn Lys Thr Gln Met Lys Asn Leu Tyr Gly Asp Ser Asn Pro
    210                 215                 220
Gln Lys Phe Thr Ser Ser Ala Asn Gly Val Thr Thr His Tyr Val Ser
225                 230                 235                 240
Gln Ile Gly Gly Phe Pro Asp Gln Thr Glu Asp Gly Gly Leu Pro Gln
                245                 250                 255
Ser Gly Arg Ile Val Val Asp Tyr Met Val Gln Lys Pro Gly Lys Thr
            260                 265                 270
Gly Thr Ile Val Tyr Gln Arg Gly Val Leu Leu Pro Gln Lys Val Trp
        275                 280                 285
Cys Ala Ser Gly Arg Ser Lys Val Ile Lys Gly Ser Leu Pro Leu Ile
    290                 295                 300
Gly Glu Ala Asp Cys Leu His Glu Lys Tyr Gly Gly Leu Asn Lys Ser
305                 310                 315                 320
Lys Pro Tyr Tyr Thr Gly Glu His Ala Lys Ala Ile Gly Asn Cys Pro
                325                 330                 335
Ile Trp Val Lys Thr Pro Leu Lys Leu Ala Asn Gly Thr Lys Tyr Arg
            340                 345                 350
Pro Pro Ala Lys Leu Leu Lys Glu Arg Gly Phe Phe Gly Ala Ile Ala
        355                 360                 365
Gly Phe Leu Glu Gly Gly Trp Glu Gly Met Ile Ala Gly Trp His Gly
    370                 375                 380
Tyr Thr Ser His Gly Ala His Gly Val Ala Val Ala Ala Asp Leu Lys
385                 390                 395                 400
Ser Thr Gln Glu Ala Ile Asn Lys Ile Thr Lys Asn Leu Asn Ser Leu
                405                 410                 415
Ser Glu Leu Glu Val Lys Asn Leu Gln Arg Leu Ser Gly Ala Met Asp
            420                 425                 430
Glu Leu His Asn Glu Ile Leu Glu Leu Asp Glu Lys Val Asp Asp Leu
        435                 440                 445
```

```
Arg Ala Asp Thr Ile Ser Ser Gln Ile Glu Leu Ala Val Leu Leu Ser
        450                 455                 460

Asn Glu Gly Ile Ile Asn Ser Glu Asp Glu His Leu Leu Ala Leu Glu
465                 470                 475                 480

Arg Lys Leu Lys Lys Met Leu Gly Pro Ser Ala Val Asp Ile Gly Asn
                485                 490                 495

Gly Cys Phe Glu Thr Lys His Lys Cys Asn Gln Thr Cys Leu Asp Arg
            500                 505                 510

Ile Ala Ala Gly Thr Phe Asn Ala Gly Glu Phe Ser Leu Pro Thr Phe
        515                 520                 525

Asp Ser Leu Asn Ile Thr Ala Ala Ser Leu Asn Asp Asp Gly Leu Asp
530                 535                 540

Asn His Thr Ile Leu Leu Tyr Tyr Ser Thr Ala Ala Ser Ser Leu Ala
545                 550                 555                 560

Val Thr Leu Met Ile Ala Ile Phe Ile Val Tyr Met Val Ser Arg Asp
                565                 570                 575

Asn Val Ser Cys Ser Ile Cys Leu
            580

<210> SEQ ID NO 24
<211> LENGTH: 584
<212> TYPE: PRT
<213> ORGANISM: Artificial Sequence
<220> FEATURE:
<223> OTHER INFORMATION: ACA33493.1 HA from B/Florida/4/2006

<400> SEQUENCE: 24

Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
                20                  25                  30

Thr Ala Thr Gln Gly Glu Val Asn Val Thr Gly Val Ile Pro Leu Thr
            35                  40                  45

Thr Thr Pro Thr Lys Ser Tyr Phe Ala Asn Leu Lys Gly Thr Arg Thr
    50                  55                  60

Arg Gly Lys Leu Cys Pro Asp Cys Leu Asn Cys Thr Asp Leu Asp Val
65                  70                  75                  80

Ala Leu Gly Arg Pro Met Cys Val Gly Thr Thr Pro Ser Ala Lys Ala
                85                  90                  95

Ser Ile Leu His Glu Val Lys Pro Val Thr Ser Gly Cys Phe Pro Ile
            100                 105                 110

Met His Asp Arg Thr Lys Ile Arg Gln Leu Pro Asn Leu Leu Arg Gly
        115                 120                 125

Tyr Glu Asn Ile Arg Leu Ser Thr Gln Asn Val Ile Asp Ala Glu Lys
    130                 135                 140

Ala Pro Gly Gly Pro Tyr Arg Leu Gly Thr Ser Gly Ser Cys Pro Asn
145                 150                 155                 160

Ala Thr Ser Lys Ser Gly Phe Phe Ala Thr Met Ala Trp Ala Val Pro
                165                 170                 175

Lys Asp Asn Asn Lys Asn Ala Thr Asn Pro Leu Thr Val Glu Val Pro
            180                 185                 190

Tyr Ile Cys Thr Glu Gly Glu Asp Gln Ile Thr Val Trp Gly Phe His
        195                 200                 205

Ser Asp Asp Lys Thr Gln Met Lys Asn Leu Tyr Gly Asp Ser Asn Pro
    210                 215                 220
```

```
Gln Lys Phe Thr Ser Ser Ala Asn Gly Val Thr Thr His Tyr Val Ser
225                 230                 235                 240
Gln Ile Gly Ser Phe Pro Asp Gln Thr Glu Asp Gly Gly Leu Pro Gln
                245                 250                 255
Ser Gly Arg Ile Val Val Asp Tyr Met Met Gln Lys Pro Gly Lys Thr
            260                 265                 270
Gly Thr Ile Val Tyr Gln Arg Gly Val Leu Leu Pro Gln Lys Val Trp
        275                 280                 285
Cys Ala Ser Gly Arg Ser Lys Val Ile Lys Gly Ser Leu Pro Leu Ile
    290                 295                 300
Gly Glu Ala Asp Cys Leu His Glu Lys Tyr Gly Gly Leu Asn Lys Ser
305                 310                 315                 320
Lys Pro Tyr Tyr Thr Gly Glu His Ala Lys Ala Ile Gly Asn Cys Pro
                325                 330                 335
Ile Trp Val Lys Thr Pro Leu Lys Leu Ala Asn Gly Thr Lys Tyr Arg
                340                 345                 350
Pro Pro Ala Lys Leu Leu Lys Glu Arg Gly Phe Phe Gly Ala Ile Ala
            355                 360                 365
Gly Phe Leu Glu Gly Gly Trp Glu Gly Met Ile Ala Gly Trp His Gly
370                 375                 380
Tyr Thr Ser His Gly Ala His Gly Val Ala Val Ala Ala Asp Leu Lys
385                 390                 395                 400
Ser Thr Gln Glu Ala Ile Asn Lys Ile Thr Lys Asn Leu Asn Ser Leu
                405                 410                 415
Ser Glu Leu Glu Val Lys Asn Leu Gln Arg Leu Ser Gly Ala Met Asp
                420                 425                 430
Glu Leu His Asn Glu Ile Leu Glu Leu Asp Glu Lys Val Asp Asp Leu
            435                 440                 445
Arg Ala Asp Thr Ile Ser Ser Gln Ile Glu Leu Ala Val Leu Leu Ser
    450                 455                 460
Asn Glu Gly Ile Ile Asn Ser Glu Asp Glu His Leu Leu Ala Leu Glu
465                 470                 475                 480
Arg Lys Leu Lys Lys Met Leu Gly Pro Ser Ala Val Glu Ile Gly Asn
                485                 490                 495
Gly Cys Phe Glu Thr Lys His Lys Cys Asn Gln Thr Cys Leu Asp Arg
            500                 505                 510
Ile Ala Ala Gly Thr Phe Asn Ala Gly Glu Phe Ser Leu Pro Thr Phe
        515                 520                 525
Asp Ser Leu Asn Ile Thr Ala Ala Ser Leu Asn Asp Asp Gly Leu Asp
    530                 535                 540
Asn His Thr Ile Leu Leu Tyr Tyr Ser Thr Ala Ala Ser Ser Leu Ala
545                 550                 555                 560
Val Thr Leu Met Leu Ala Ile Phe Ile Val Tyr Met Val Ser Arg Asp
                565                 570                 575
Asn Val Ser Cys Ser Ile Cys Leu
                580
```